United States Patent
Godoy et al.

(10) Patent No.: US 10,564,308 B1
(45) Date of Patent: Feb. 18, 2020

(54) ELECTRON PARAMAGNETIC RESONANCE (EPR) TECHNIQUES AND APPARATUS FOR PERFORMING EPR SPECTROSCOPY ON A FLOWING FLUID

(71) Applicant: MICROSILICON INC., Katy, TX (US)

(72) Inventors: Manuel Godoy, Houston, TX (US); Aydin Babakhani, Houston, TX (US); Omar Kulbrandstad, Katy, TX (US); John Lovell, Houston, TX (US)

(73) Assignee: MICROSILICON INC., Katy, TX (US)

( * ) Notice: Subject to any disclaimer, the term of this patent is extended or adjusted under 35 U.S.C. 154(b) by 31 days.

(21) Appl. No.: 15/875,823

(22) Filed: Jan. 19, 2018

Related U.S. Application Data

(60) Provisional application No. 62/448,095, filed on Jan. 19, 2017.

(51) Int. Cl.
  *G01V 3/14* (2006.01)
  *E21B 49/08* (2006.01)
  *G01N 24/10* (2006.01)

(52) U.S. Cl.
  CPC ............. *G01V 3/14* (2013.01); *E21B 49/08* (2013.01); *G01N 24/10* (2013.01)

(58) Field of Classification Search
  None
  See application file for complete search history.

(56) References Cited

U.S. PATENT DOCUMENTS

| | | | |
|---|---|---|---|
| 4,803,624 A | 2/1989 | Pilbrow et al. | |
| 4,888,554 A | 12/1989 | Hyde et al. | |
| 5,233,303 A | 8/1993 | Bales et al. | |
| 6,051,535 A | 4/2000 | Bilden et al. | |

(Continued)

FOREIGN PATENT DOCUMENTS

WO 2016187300 A1 11/2016

OTHER PUBLICATIONS

Biktagirov et al., "Electron Paramagnetic Resonance Study of Rotational Mobility of the Vanadyl Porphyrin Complexes in Crude Oil Asphaltenes: Probing the Effect of the Thermal Treatment of Heavy Oils," Energy & Fuels, 2014, 28, pp. 6683-6687.

(Continued)

*Primary Examiner* — Douglas X Rodriguez
(74) *Attorney, Agent, or Firm* — Patterson + Sheridan, LLP

(57) ABSTRACT

Certain aspects of the present disclosure provide methods and apparatus for performing electron paramagnetic resonance (EPR) spectroscopy on a fluid from a flowing well, such as fluid from hydrocarbon recovery operations flowing in a downhole tubular, wellhead, or pipeline. One example method generally includes, for a first EPR iteration, performing a first frequency sweep of discrete electromagnetic frequencies on a cavity containing the fluid; determining first parameter values of reflected signals from the first frequency sweep; selecting a first discrete frequency corresponding to one of the first parameter values that is less than a threshold value; activating a first electromagnetic field in the fluid at the first discrete frequency; and while the first electromagnetic field is activated, performing a first DC magnetic field sweep to generate a first EPR spectrum.

20 Claims, 18 Drawing Sheets

(56) References Cited

U.S. PATENT DOCUMENTS

| | | | |
|---|---|---|---|
| 6,346,813 | B1 | 2/2002 | Kleinberg |
| 6,573,715 | B2 | 6/2003 | King et al. |
| 7,683,613 | B2 | 3/2010 | Freedman et al. |
| 7,868,616 | B2 | 1/2011 | White et al. |
| 8,125,224 | B2 | 2/2012 | White et al. |
| 8,210,826 | B2 | 7/2012 | Freeman |
| 8,212,563 | B2 | 7/2012 | White et al. |
| 8,829,904 | B2 | 9/2014 | White et al. |
| 9,103,261 | B1 | 8/2015 | White et al. |
| 9,689,954 | B2 | 6/2017 | Yang et al. |
| 2004/0140800 | A1* | 7/2004 | Madio .............. G01N 24/081 324/303 |
| 2009/0219019 | A1* | 9/2009 | Taherian ........... G01N 24/081 324/303 |
| 2012/0087867 | A1 | 4/2012 | McCamey et al. |
| 2013/0093424 | A1 | 4/2013 | Blank et al. |
| 2014/0097842 | A1* | 4/2014 | Yang ................. G01R 33/60 324/316 |
| 2015/0185255 | A1 | 7/2015 | Eaton et al. |
| 2015/0185299 | A1 | 7/2015 | Rinard et al. |
| 2016/0223478 | A1 | 8/2016 | Babakhani et al. |

OTHER PUBLICATIONS

Chzhan, M., et al., "A Tunable Reentrant Resonator with Transverse Orientation of Electric Field for in Vivo EPR Spectroscopy," Journal of Magnetic Resonance 137, 373-378 (1999).

Cole, K. S. et al., "Dispersion and Absorption in Dielectrics," J. Appl. Phys., 9, 341-351 (1941).

Crude Oil Emulsions—Composition, Stability, and Characterization, Edited by Manar El-Sayed Abdel, published by Intech, 2012, Croatia. ISBN 978-953-51-0220-5.

G.R. Eaton, S.S. Eaton, D.P. Barr, and R.T. Weber, Quantitative EPR, Vienna: Springer, 2010.

Mamin, G. V., et al., "Toward the Asphaltene Structure by Electron Paramagnetic Resonance Relaxation Studies at High Fields (3.4 T)," Energy Fuels, 2016, 30 (9), pp. 6942-6946.

"Measurement of Complex Permittivity and Permeability through a Cavity Perturbation Measurement," Master's Thesis in Applied Physics by Tomas Rydholm, Chalmers University of Technology, Sweden, 2015.

Sheu, E. Y., et al., "A dielectric relaxation study of precipitation and curing of Furrial crude oil," Fuel, vol. 85, (2006) pp. 1953-1959.

Sundramoorthy et al., "Orthogonal Resonators for Pulse In Vivo Electron Paramagnetic Imaging at 250MHz," Journal Magnetic Resonance, vol. 240, pp. 45-51 (Mar. 2014).

Tukhvatullina, A. Z,, et al., "Supramolecular Structures of Oil Systems as the Key to Regulation of Oil Behavior," Petroleum & Environmental Biotechnology, <http://dx.doi.org/10.4172/2157-7463.1000152> (2013).

Adel M. Elsharkawy, et al., "Characterization of Asphaltenes and Resins Separated from Water-in-Oil Emulsions," Journal Petroleum Science and Technology, vol. 26, 2008—Issue 2, 22 Pages.

Freed, J. H., et al., "Theory of Linewidths in Electron Spin Resonance Spectra," The Journal of Chemical Physics, vol. 39, (1963), pp. 326-348.

Goual, L., "Impedance Spectroscopy of Petroleum Fluids at Low Frequency," Energy and Fuels, 23, (2009), pp. 2090-2094.

H. Yokoyama and T. Yoshimura, "Combining a magnetic field modulation coil with a surface-coil-type EPR resonator," Applied Magnetic Resonance, vol. 35, Issue 1, pp. 127-128 (Nov. 2008).

J. A. Weil and J. R. Bolton, Electron Paramagnetic Resonance: Elementary Theory and Practical Applications, 2nd Ed., Hoboken, NJ: John Wiley & Sons, 2007, pp. 33-35.

L. Montenari, et al., "Asphaltene Radicals and their Interaction with Molecular Oxygen: an EPR Probe of their Molecular Characteristics and Tendency to Aggregate," Appl. Magn. Reson., 1998, 14, pp. 81-82.

Lesaint, C., et al., "Dielectric Properties of Asphaltene Solutions: Solvency Effect on Conductivity," Energy&Fuels, 27 (1), (2013), pp. 75-81.

Marcela Espinosa P., et al., "Electron Spin Resonance and Electronic Structure of Vanadyl—Porphyrin in Heavy Crude Oils," Inorg. Chem., 2001, 40, pp. 4543-4549.

S. Kokal et al., "Asphaltene Precipitation in a Saturated Gas-Cap Reservoir", Society of Petroleum Engineers Inc., SPE 89967 (2004) pp. 1-9.

S. Petryakov et al., "Single Loop—MultiGap Resonator for Whole Body EPR Imaging of Mice at 1.2 GHz," Journal of Magnetic Resonance, v188(1), pp. 1-13 (Sep. 2007).

Sanjay Misra, et al., "Successful Asphaltene Cleanout Field Trial in On-Shore Abu Dhabi Oil Fields," SPE 164175-MS, Mar. 2013, pp. 1-5.

Sheu, E. Y., et al., "Asphaltene self-association and precipitation in solvents and AC conductivity measurements," Asphaltenes, Heavy Oils and Petroleomics, Springer: New York, 2007, pp. 259-260.

Sheu, E. Y., et al., "Frequency-dependent conductivity of Utah crude oil asphaltene and deposit," Energy Fuels, 18, (2004), pp. 1531-1534.

Teh Fu Yen, et al., "Investigation of the Nature of Free Radicals in Petroleum Asphaltenes and Related Substances by Electron Spin Resonance," Analytical Chemistry, 1962, 34(6), pp. 694-700.

\* cited by examiner

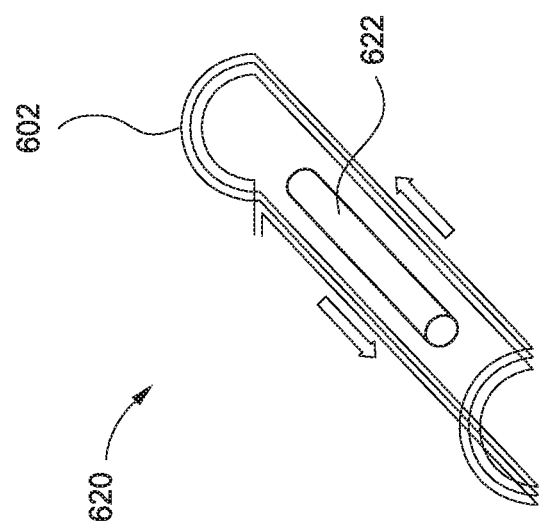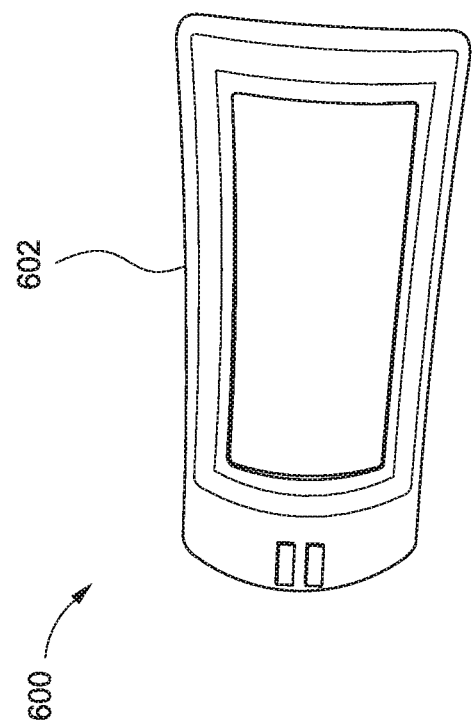
FIG. 6

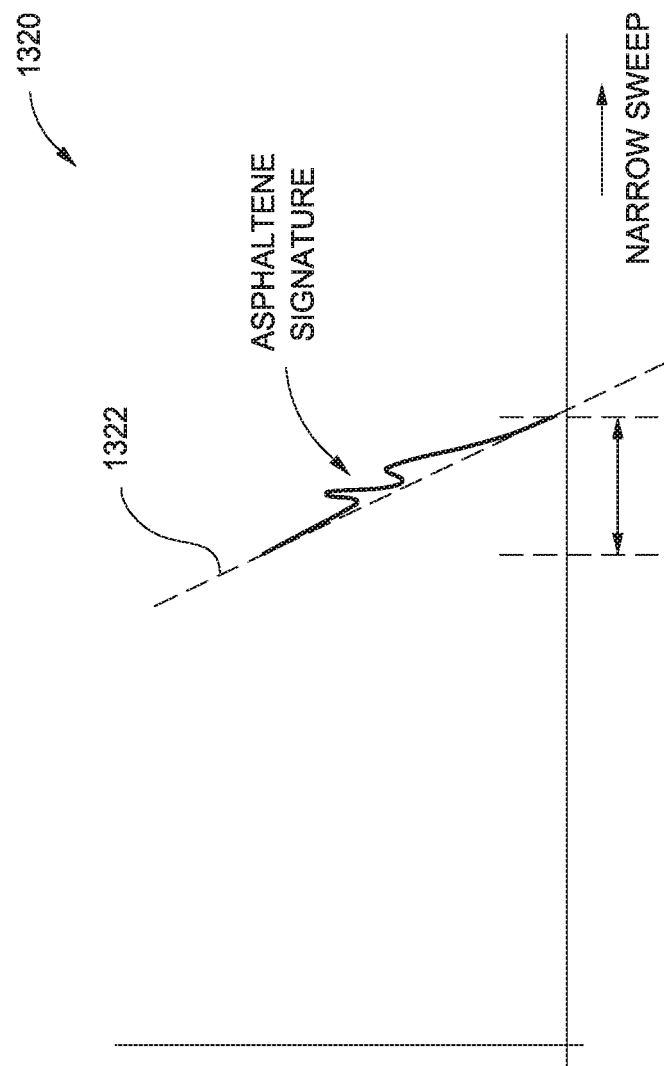

ELECTRON PARAMAGNETIC RESONANCE (EPR) TECHNIQUES AND APPARATUS FOR PERFORMING EPR SPECTROSCOPY ON A FLOWING FLUID

CLAIM OF PRIORITY UNDER 35 U.S.C. § 119

This application claims priority to U.S. Provisional Patent Application No. 62/448,095, entitled "Electron Paramagnetic Resonance (EPR) Sensor Based on Automated Closed-Loop Impedance Matching" and filed Jan. 19, 2017, herein incorporated by reference in its entirety.

BACKGROUND

Field of the Disclosure

The present disclosure generally relates to electron paramagnetic resonance (EPR) and, more specifically, to utilizing EPR methods and systems to detect the characteristics of materials, for example, in wells, pipelines, or formations, such as for flow assurance or logging.

Relevant Background

Electron paramagnetic resonance (EPR), also referred to as electron spin resonance (ESR), is a spectroscopic and imaging technique that is capable of providing quantitative information regarding the presence and concentration of a variety of paramagnetic species within a sample under test. The valence electrons of a paramagnetic species possess unpaired spin angular momentum and, thus, have net magnetic moments that tend to align along an externally applied magnetic field. This alignment process is known as paramagnetization. EPR is a measurement technique that relies on the external manipulation of the direction of this electron paramagnetization, also referred to as a net electronic magnetic moment. In a typical EPR experiment, a polarizing static magnetic field $B_0$ (also referred to as a DC magnetic field) is applied to a sample to align the magnetic moments of the electrons along the direction of the magnetic field $B_0$. Then, a high-frequency oscillating magnetic field $B_1$, often referred to as the transverse magnetic field or the radio frequency (RF) magnetic field, is applied along a direction that is perpendicular to the polarizing field $B_0$. Usually, the oscillating field $B_1$ is generated using a microwave resonator (fed via a coil or a transmission line) and is designed to excite the unpaired electrons by driving transitions between the different angular momentum states of the unpaired electron(s).

EPR technology is based on the interaction of these electron spins with the applied RF (e.g., microwave) electromagnetic fields in the presence of the external static (DC) magnetic field. EPR data provides valuable information about electronic structures and spin interactions in paramagnetic materials. EPR has found wide-ranging applications in various science and engineering technology areas, such as studying chemicals involving free radicals or transition metal ions.

The major components of an EPR spectroscope are typically similar. For example, U.S. Pat. No. 4,803,624 to Pilbrow et al., entitled "Electron Spin Resonance Spectrometer" and issued Feb. 7, 1989, teaches an electron spin resonance spectrometer with a magnetic sweep from 0 to 0.15 tesla (T) operating in the range of 1 to 5 GHz with a loop-gap resonator containing a cavity to hold a fluid sample. This spectrometer uses a circulator to measure the reflected microwave signal from the resonator, the same as in most commercially available EPR spectrometers. Microwave circuit components (e.g., an isolator, circulator, power dividers, variable attenuator, and directional couplers) are arranged in a microwave bridge connected by microstrip transmission lines. External components, such as the microwave source and loop-gap resonator, are connected via SMA coaxial connectors. External magnetic fields can be provided by permanent magnets, electromagnets, or a combination of both.

It is known that the resonant frequency of a fluid-filled cavity changes depending on the fluid properties therein, as does the efficiency of the coupling of the electromagnetic field to the cavity. The pertinent electrical parameters of the cavity are its dielectric and conductivity properties, which combine into an effective permeability according to the formula $\varepsilon + i\sigma/\omega$, where $\varepsilon$ is the ratio of electrical displacement field to electric field, $\sigma$ is the conductivity, and $e^{-i\omega t}$ is the variation of the field in time (i.e., $\omega$ is the radial frequency, equal to $2\pi f$ where f is excitation frequency). The displacement field can be out of phase with the electric field, in which case $\varepsilon$ can be viewed as a complex number, or else the imaginary component of $\varepsilon$ can be incorporated into the conductivity. In this text, and as is common in the electromagnetic community, the term "permittivity" is used to refer to both the complex value $\varepsilon + i\sigma/\omega$, and also to just the dielectric component, $\varepsilon$. The intended meaning will be clear to a person having ordinary skill in the art. The magnetic properties of the medium are given by the permeability $\mu$, which is the ratio of magnetic flux intensity B to the magnetic field intensity H. In air, the permeability is denoted $\mu_0$. More generally one can write $\mu = \mu_0 (1+\chi)$, where $\chi$ is termed the "susceptibility." The B and H fields may be out of phase, in which case $\mu$ and $\chi$ are also complex numbers. The imaginary component of $\chi$ is called its "AC magnetic susceptibility." A classical interpretation of the EPR signal is that the applied magnetic field induces a change in the AC magnetic susceptibility. Knowledge of $\varepsilon$, $\sigma$, and $\mu$ can be used to identify fluid components; for example, $\varepsilon$ is about 80 in water, 2-5 in oil, and 1 in a gas. $\sigma$ will be virtually zero in hydrocarbons, but nonzero if there is a mix of salty brine water along with the oil. $\mu$ will typically be close to 1, but magnetic particles (e.g., from the wall of iron tubulars or from some minerals) can increase $\mu$.

As noted, for example, by U.S. Pat. No. 4,888,554 to Hyde et al., entitled "Electron Paramagnetic Resonance (EPR) Spectrometer" and issued Dec. 19, 1989 (hereinafter "Hyde '554"), part of the reflected signal which is in phase with the RF magnetic field gives the absorption spectrum, whereas that part which is out of phase gives a dispersion spectrum. The absorption spectrum typically has the more useful information for paramagnetic analysis. Hyde '554 also discloses that a circuit can be added to automatically lock the RF frequency to the cavity resonance frequency.

The incoming RF signal will typically be transported to the resonator via a coax cable that has a certain characteristic impedance (e.g., 50Ω). The resonator itself has a different impedance, which will be some complex number representing a mostly inductive load. That impedance depends on the structural design of the resonator, as well as the contents of the fluid therein. An exemplary EPR design will include an impedance matching circuit that can vary one or more parameters so that the combination of the impedance matching circuit and the resonator will be a load impedance adjusted to match that of the impedance looking back into the transmit path for a particular frequency or range of frequencies. This matching will minimize reflections in the circuit path from the resonator. In a typical embodiment, the impedance matching circuit will vary the capacitance using one or more components, such as a varactor, whose capacitance can be set by varying an external parameter (e.g., an applied DC voltage). Capacitance is but one aspect of impedance, so it is fair to describe the impedance matching circuit as one which is varying its impedance. The impedance matching process is thus an impedance sweep to match the impedance of the incoming coax to the impedance of the combination of the impedance matching circuit and the resonator. The value chosen for that impedance will vary according to the electromagnetic properties of the fluid in the resonator cavity.

Until recently, EPR spectrometers comprised components that were expensive and large in both weight and physical dimensions. Because of this high cost ($500 k), large weight (100 kg), and large size (1 m$^3$), EPR spectrometers were unsuitable for field use in the oil industry, such as for application inside wellbores, at wellheads, or along pipelines.

Smaller, more portable devices have been introduced in the last few years, and these can now provide wellsite solutions by taking samples of fluids from the wellbore. The evaluation is performed by inserting the fluid sample into a measurement cavity within the portable EPR device. Spectroscopic information for that fluid is then available to the operator, providing answers within minutes of taking the sample, without the historical requirement to ship the sample to a chemical laboratory for analysis offsite.

Although not specifically targeted to the oilfield, patents disclosing such smaller devices include U.S. Pat. No. 8,212,536 to White et al., entitled "Method and Apparatus for In-situ Measurement of Soot by Electron Spin Resonance (ESR) Spectrometry" and issued Jul. 3, 2012; U.S. Pat. No. 8,829,904 to White et al., entitled "Method of and Apparatus for In-situ Measurement of Degradation of Automotive Fluids and the Like by Micro-electron Spin Resonance (ESR) Spectrometry" and issued Sep. 9, 2014; U.S. Pat. No. 7,868,616 to White et al., entitled "Method of and Apparatus for In-situ Measurement of Changes in Fluid Composition by Electron Spin Resonance (ESR) Spectrometry" and issued Jan. 11, 2011; and U.S. Pat. No. 5,233,303 to Bales et al., entitled "Portable Dedicated Electron Spin Resonance Spectrometer" and issued Aug. 3, 1993 (hereinafter "Bales '303"). The entire contents of these four patents are herein incorporated by reference.

Subsequently, it has been determined that the physical characteristics of the spectrometer were not the only hurdles to installation for well or pipeline applications. By taking measurements every few hours on a portable device at the wellsite, it is now known that the EPR properties of an oilfield fluid can change dramatically, particularly during a chemical treatment or clean-up of the well. It has also been determined that exposing a well fluid to oxygen can change the fluid's EPR response. EPR responses are further known to change based on the fluid temperature and pressure. Given the EPR response at wellhead temperatures and pressures and a separate pressure, volume, and temperature (PVT) analysis of the fluid, it may be possible to estimate EPR responses upstream (e.g., deeper in the well). However, the measurement cavity in the portable EPR devices is not in pressure communication with the wellhead or surface facilities. Instead, those devices operate by taking a sample of fluid from the wellhead (or a pipeline exit), transferring that sample to the measurement device, and then inserting the sample into the device cavity. Such fluid samples are therefore not at the same pressure, temperature, and other conditions as these samples would be downhole, in the wellhead, or in the surface production pipelines. Also, those samples are typically exposed to the atmosphere as part of the transition from wellhead or pipeline infrastructure to the measurement device. Furthermore, there is still a delay between taking the fluid samples and performing EPR measurements thereon; thus, the measurement of such samples is not in real-time as the fluid is flowing in the tubular. This has created the need for an EPR device that could be integrated into oilfield apparatus and that could make continuous EPR measurements of flowing fluid under actual conditions, without exposing that fluid to the air and without bringing the typically multiphase well fluid to atmospheric temperature and pressure.

It is known that in multiphase flow, the fluid may traverse in different flow regimes (e.g., bubble flow, slug flow, and emulsion flow for two liquids and bubble flow, dispersed bubble flow, plug flow, slug flow, froth flow, mist flow, churn flow, and annular flow for gas-liquid combinations). It is also known that for some of these flow regimes, turbulizers can be included in the tubular to make downstream cross-sections of the pipe more representative of the average flow (e.g., for sampling). For slug flow, however, turbulizers are less useful: the first fluid will not become blended with the second. Rather, the two fluids will stay as separate components travelling along the wellbore. Such a scenario is not uncommon for applications of enhanced oil recovery when the wellhead may see many feet of injected water, followed by a few feet of oil, and then many more feet of water.

In the case of wellbore cleanouts for asphaltene or scale removal, large volumes of solvents, surfactants, or dispersants may be pumped into a wellbore and then retrieved back to surface when the well is put back online. In this scenario, a first fluid will be flowing for many minutes or hours before a more representative sample of reservoir fluid returns to the surface.

As noted above, the electrical properties of a resonator cavity will change dependent upon the fluid therein, so for a cavity continually being refreshed with fluid from a flowing wellbore, these parameters can change quickly as different fluids reach the wellhead. This leads to the desired capability of quickly changing the frequency of the applied RF magnetic field to keep the cavity at or near resonance. Similarly, it may be desirable to quickly update any impedance match to the cavity.

None of the cited patent references above anticipate real-time measurements of a flowing fluid with rapidly changing fluid properties, nor do these references anticipate maintaining the fluid in its original state of temperature and pressure and with no opportunity for fluid spectral changes as a result of exposure to oxygen. Accordingly, these references and the teachings therein are not applicable to many oilfield applications.

SUMMARY

Certain aspects of the present disclosure generally relate to using electron paramagnetic resonance (EPR) to analyze a flow system.

Certain aspects of the present disclosure provide a method of performing EPR spectroscopy on a fluid from a flowing well. The method generally includes, for a first EPR iteration, performing a first frequency sweep of discrete electromagnetic frequencies on a cavity containing the fluid; determining first parameter values of reflected signals from the first frequency sweep; selecting a first discrete frequency corresponding to one of the first parameter values that is less than a threshold value; activating a first electromagnetic field in the fluid at the first discrete frequency; and while the first electromagnetic field is activated, performing a first DC magnetic field sweep to generate a first EPR spectrum.

Certain aspects of the present disclosure provide an EPR spectrometer for performing EPR spectroscopy on a fluid from a flowing well. The EPR spectrometer generally includes a tube having a cavity capable of receiving the fluid; a magnetic field generator configured to generate a DC magnetic field in the fluid during operation of the EPR spectrometer; transmit circuitry configured to generate a radio frequency (RF) signal; a resonator coupled to the transmit circuitry and configured to convert the RF signal into an RF magnetic field in the fluid during the operation of the EPR spectrometer; receive circuitry configured to receive and process reflected signals from the fluid via the resonator; and at least one processor coupled to the magnetic field generator, the transmit circuitry, and the receive circuitry. For a first EPR iteration, the at least one processor is generally configured to control the transmit circuitry to perform a first frequency sweep of discrete electromagnetic frequencies on the cavity containing the fluid; to determine first parameter values of reflected signals from the first frequency sweep; to select a first discrete frequency corresponding to one of the first parameter values that is less than a threshold value; to control the transmit circuitry to activate a first electromagnetic field in the fluid at the first discrete frequency; and to control the magnetic field generator, while the first electromagnetic field is activated, to perform a first DC magnetic field sweep to generate a first EPR spectrum.

Certain aspects of the present disclosure provide a non-transitory computer-readable medium storing instructions that, when executed on a processor, perform operations for performing EPR spectroscopy on a fluid from a flowing well. For a first EPR iteration, the operations generally include performing a first frequency sweep of discrete electromagnetic frequencies on a cavity containing the fluid; determining first parameter values of reflected signals from the first frequency sweep; selecting a first discrete frequency corresponding to one of the first parameter values that is less than a threshold value; activating a first electromagnetic field in the fluid at the first discrete frequency; and while the first electromagnetic field is activated, performing a first DC magnetic field sweep to generate a first EPR spectrum.

Certain aspects of the present disclosure provide a method of performing EPR spectroscopy on a fluid from a flowing well. The method generally includes activating a magnetic field generator to generate a DC magnetic field at a first magnetic flux density in a cavity containing the fluid; while the DC magnetic field is activated at the first magnetic flux density, performing at least one of: a frequency sweep to determine a frequency for generating a radio frequency (RF) magnetic field in the fluid; or an impedance sweep to set an impedance of an impedance matching circuit associated with the generation of the RF magnetic field; and sweeping the activated DC magnetic field from the first magnetic flux density to a second magnetic flux density using at least one of the determined frequency or the impedance to generate an EPR spectrum.

Certain aspects of the present disclosure provide an EPR spectrometer for performing EPR spectroscopy on a fluid from a flowing well. The EPR spectrometer generally includes a tube capable of receiving the fluid; a magnetic field generator configured to generate a DC magnetic field in the fluid during operation of the EPR spectrometer; transmit circuitry configured to generate a radio frequency (RF) signal; a resonator coupled to the transmit circuitry and configured to convert the RF signal into an RF magnetic field in the fluid during the operation of the EPR spectrometer; impedance matching circuitry coupled between the transmit circuitry and the resonator; receive circuitry configured to receive and process reflected signals from the fluid via the resonator; and at least one processor coupled to the magnetic field generator, the transmit circuitry, and the receive circuitry. The at least one processor is generally configured to activate the magnetic field generator to generate the DC magnetic field at a first magnetic flux density; to control, while the DC magnetic field is activated at the first magnetic flux density, at least one of: the transmit circuitry to perform a frequency sweep to determine a frequency for generating the RF magnetic field in the fluid; or the impedance matching circuitry to perform an impedance sweep to set an impedance of the impedance matching circuitry associated with the generation of the RF magnetic field; and to control the magnetic field generator to sweep the activated DC magnetic field from the first magnetic flux density to a second magnetic flux density using at least one of the determined frequency or the impedance to generate an EPR spectrum.

Certain aspects of the present disclosure provide a non-transitory computer-readable medium storing instructions that, when executed on a processor, perform operations for performing EPR spectroscopy on a fluid from a flowing well. The operations generally include activating a magnetic field generator to generate a DC magnetic field at a first magnetic flux density; while the DC magnetic field is activated at the first magnetic flux density, performing at least one of: a frequency sweep to determine a frequency for generating a radio frequency (RF) magnetic field in the fluid; or an impedance sweep to set an impedance of an impedance matching circuit associated with the generation of the RF magnetic field; and sweeping the activated DC magnetic field from the first magnetic flux density to a second magnetic flux density using at least one of the determined frequency or the impedance to generate an EPR spectrum.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

FIG. 6 is an illustration of a coil on a flexible circuit that can create a modulated magnetic field in a resonator cavity, in accordance with certain aspects of the present disclosure.

FIG. 13B is a graph of an example EPR response over a relatively narrower magnetic sweep range associated with asphaltene in crude oil, in accordance with certain aspects of the present disclosure.

DETAILED DESCRIPTION

Figure 1:
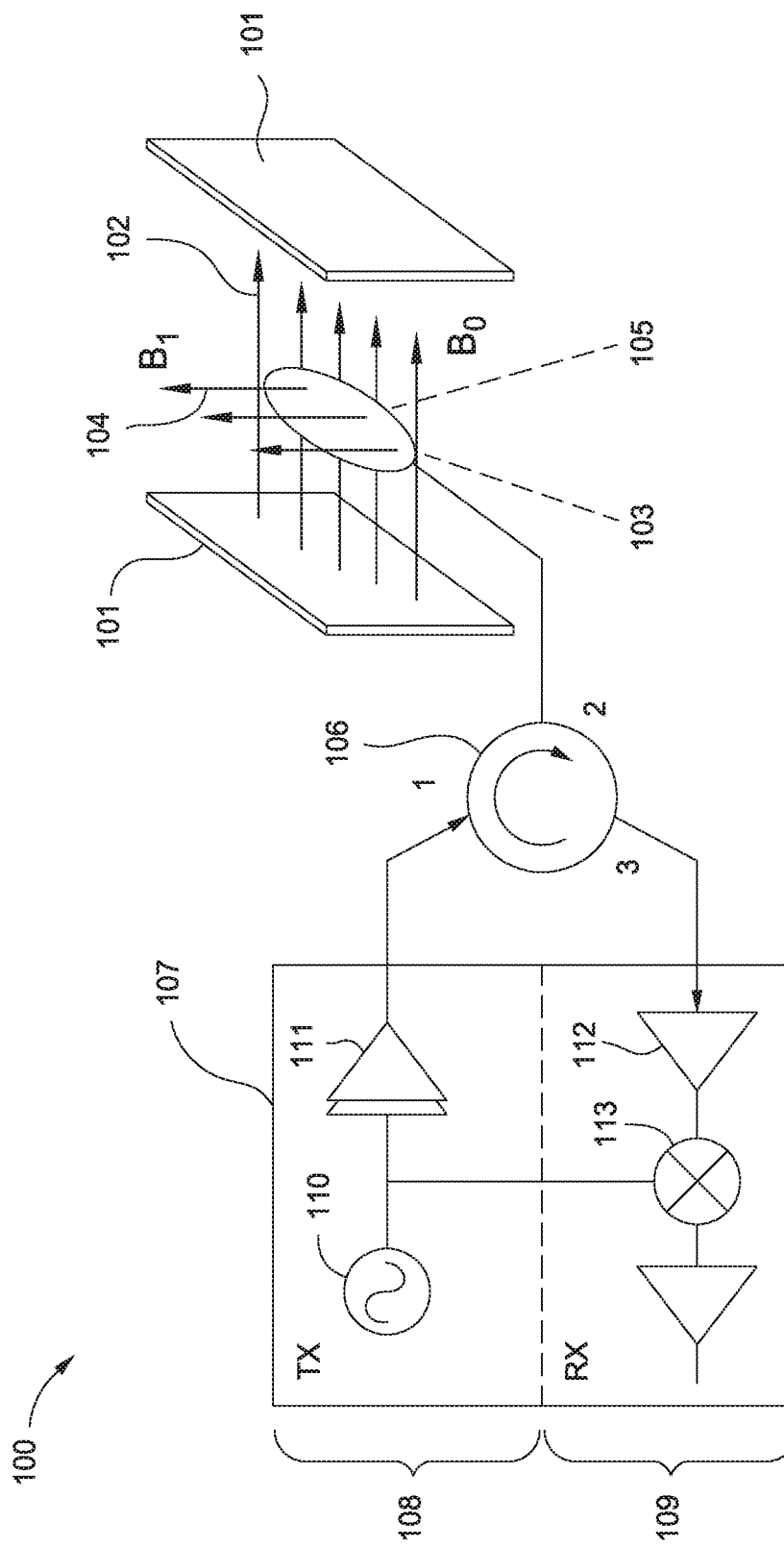
FIG. 1 is a block diagram of an electron paramagnetic resonance (EPR) spectrometer, in accordance with certain aspects of the present disclosure.

Certain aspects of the present disclosure provide methods and apparatus for performing electron paramagnetic resonance (EPR) spectroscopy on a fluid.

Refer now to the drawings wherein depicted elements are not necessarily shown to scale and wherein like or similar elements are designated by the same reference numeral through the several views.

Referring to the illustrations in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art at the time of filing the present disclosure.

It is to be understood that both the foregoing general description and the following detailed description are exemplary and explanatory only, and are not restrictive of the invention, as claimed. In this application, the use of the singular includes the plural, the word "a" or "an" means "at least one," and the use of "or" means "and/or," unless specifically stated otherwise. Furthermore, the use of the term "including," as well as other forms, such as "includes" and "included," is not limiting. Also, terms such as "element" or "component" encompass both elements or components comprising one unit and elements or components that comprise more than one unit, unless specifically stated otherwise.

Electron paramagnetic resonance (EPR) is a known technique to derive paramagnetic characteristics of materials by exposing these materials to a combination of magnetic and electromagnetic fields that induces resonance of unpaired electrons within the materials. Discussion of EPR principles and techniques can be found in J. A. Weil and J. R. Bolton, *Electron Paramagnetic Resonance: Elementary Theory and Practical Applications*, $2^{nd}$ Ed., Hoboken, N.J.: John Wiley & Sons, 2007; Gilbert et al., Electron Paramagnetic Resonance, Volume 20, The Royal Society of Chemistry, Cambridge UK 2007; A. Schweiger and G. Jeschke, *Principles of Pulse Electron Paramagnetic Resonance*, Oxford University Press, 2001; and G. R. Eaton, S. S. Eaton, D. P. Barr, and R. T. Weber, *Quantitative EPR*, Vienna: Springer, 2010.

According to certain aspects of the present disclosure, the steps generally involved in EPR measurement may include first estimating the resonant frequency of an enclosure cavity containing the wellbore fluid sample, exciting a uniform magnetic field, $B_1$, at or near the resonant frequency by coupling against an incoming radio frequency (RF) field, and then applying a strong static magnetic field, $B_0$, that is oriented largely perpendicular to the first magnetic field. The strength of that DC magnetic field may then be swept to create the desired EPR spectrum based on reflection. For a given paramagnetic species, the range of the magnetic sweep involved scales with the excitation frequency.

Application of EPR to the oilfield industry has been disclosed in U.S. Patent Publication No. 2016/0223478 to Babakhani et al., entitled "EPR Systems for Flow A Assurance and Logging" and filed Sep. 25, 2014, the entire contents of which are incorporated by reference herein. Babakhani et al. point out that until recently, EPR spectrometers comprised components that were expensive, heavy, and large. More portable devices have been disclosed in the past few years. In particular, U.S. Pat. No. 9,689,954 to Yang et al., entitled "Integrated Electron Spin Resonance Spectrometer" and issued Jun. 27, 2017, discloses a technique to significantly reduce the size of the spectrometer by incorporating the microwave circuitry onto an integrated circuit. Such size spectrometer reduction may permit using EPR sensors in applications that were previously unachievable due to size and portability constraints. For example, at the wellsite, the resulting sensor can detect contributions from heavy oil, hydrocarbons, asphaltenes, vanadium, resins, drilling fluid, mud, wax deposits, and the like.

Although such portable EPR devices have been developed, it has been determined that the physical characteristics of the spectrometer were not the only hurdles to installation for well or pipeline applications. By taking measurements every few hours on a portable EPR device at the wellsite, it is now known that the EPR properties of an oilfield fluid can change dramatically, particularly during a chemical treatment or clean-up of the well. It has also been determined that exposing a well fluid to oxygen (e.g., in the air) can change the fluid's EPR response. EPR responses are also known to change based on the fluid temperature and pressure.

This has created the need for a device that can be integrated into oilfield apparatus and that can make continuous EPR measurements of a multiphase (flowing) fluid, without exposing that fluid to the air, and without bringing the well fluid to atmospheric temperature and pressure. Certain aspects of the present disclosure provide techniques and apparatus for such an EPR device.

FIG. 1 is a block diagram of an example EPR spectrometer 100, in accordance with certain aspects of the present disclosure. The EPR spectrometer 100 may generally use building blocks similar to those of a traditional EPR spectrometer. For example, the EPR spectrometer 100 may include one or more magnets 101, a resonator 103, and a transceiver 107, which includes both transmit (TX) circuitry 108 and receive (RX) circuitry 109 (also referred to as a transmitter and a receiver, respectively).

For certain aspects, the transceiver 107 may be a microwave transceiver, operating at frequencies between 300 MHz and 300 GHz, for example. The TX circuitry 108 may include a frequency synthesizer 110 and a power amplifier 111 coupled between the output of the frequency synthesizer 110 and a (e.g., port 1) of the circulator 106. The TX circuitry 108 is coupled to the resonator 103 via a circulator 106, so that the energy of the source transmission does not overwhelm the sensitive circuits of the RX circuitry 109. The output of the circulator 106 passes to the resonator 103, which creates a radio frequency (RF) electromagnetic field 104 ($B_1$ field) whose magnetic component is largely perpendicular to that of the static DC magnetic field 102 ($B_0$ field or Zeeman field).

A magnetic field generator provides the DC magnetic field 102 utilizing magnets 101, coils, or the like. The resonator 103 and sample chamber therein are placed inside the magnets 101 and/or coils that generate the DC magnetic field $B_0$. The sample chamber is designed to allow fluids to flow therethrough. The fluid flow might be that of a full tubular in wellsite equipment or a sidestream to which a subset of the main flow has been directed. In a downhole apparatus, the fluid flow might be that coming from a specific interval of the reservoir, such as directed by a downhole control valve or similar device. The presence of the Zeeman field introduces an energy difference $\Delta E$ between the two spin states of an unpaired electron: parallel and anti-parallel to $B_0$, with $\Delta E$ being proportional to $B_0$. At its resonant frequency, the resonator 103 produces the RF magnetic field $B_1$. Using the notation h for the Planck constant, then at that RF frequency (f) where hf equals $\Delta E$ (i.e., the Larmor frequency), spin transitions between the two up and down spin states occur, resulting in absorption of RF energy in the sample. In a reflection-type resonator, this results in a change in the level of reflected power from the resonator. This reflected power from the resonator is coupled to the receiver via the circulator 106 (at port 3). For certain aspects, the receiver may include a low noise amplifier (LNA) 112, a mixer 113 coupled to the output of the LNA 112 and the output of the frequency synthesizer 110, and an amplifier 114 coupled to the output of the mixer 113.

As noted by International Patent Application Publication No. 2016187300 to Babakhani et al., entitled "Electron Paramagnetic Resonance (EPR) Systems with Active Cancellation" and filed May 18, 2016, the circulator might not provide complete isolation between the TX and RX circuitry, in which case an active cancellation component may be added to the EPR spectrometer, as described therein. The entire contents of WO 2016187300 are herein incorporated by reference.

The resonator 103 may be excited with continuous wave or pulsed excitation. In one aspect, the EPR sensor is a sensor that operates at 1 GHz or higher. In other aspects, the EPR sensor may operate at lower frequencies. For certain aspects, the EPR sensor may operate in the range of 3-5 GHz.

Figure 2A:
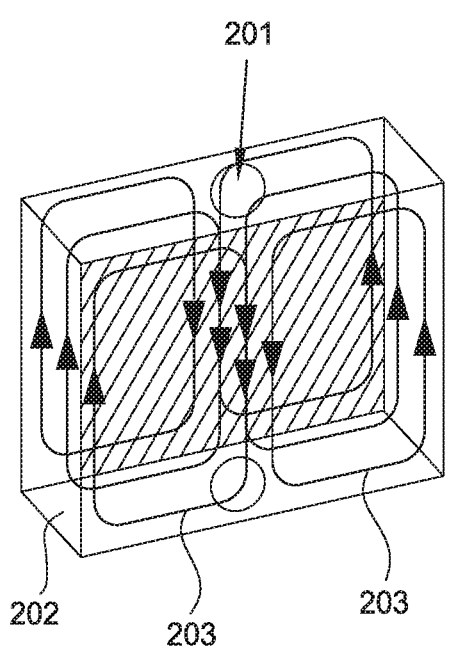
FIGS. 2A and 2B conceptually illustrate magnetic and electrical components, respectively, of a microwave field in an example EPR resonator, in accordance with certain aspects of the present disclosure.
Figure 2B:
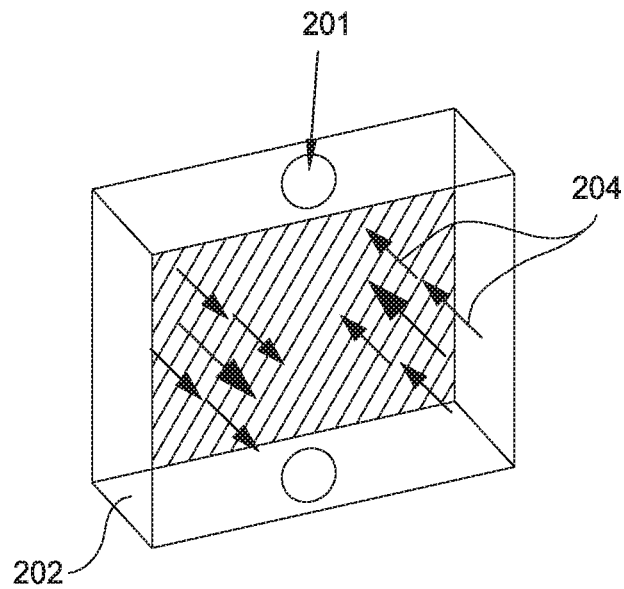

The design and construction of the resonator and its resonant cavity are important. The resonant cavity may most likely be designed such that the amplitude of the electrical component will be typically large over some region of the resonator, while the magnetic field is large over a different region. For example, Eaton (op. cit.) gives this comparison of magnetic and electric fields in the typical cavity of some commercial EPR systems, which are represented in FIGS. 2A and 2B. FIG. 2A illustrates a sample cavity 201 in an example resonator 202 with microwave magnetic field lines 203 depicted. FIG. 2B illustrates the same resonator 202 with microwave electric field lines 204 portrayed.

The sample (e.g., a flowing fluid from hydrocarbon recovery operations) should ideally be inserted into the region with large magnetic field, as opposed to the region with large electric field. This is particularly important in the case of oilfield flow sensing, because the fluid will typically contain at least some component of brine, which is electrically conductive. Oilfield fluid might also be corrosive (e.g., if acids are pumped into the well) and/or erosive (e.g., if there is a significant quantity of solids produced from the well or scraps of metal, etc., from tubular walls). Conventionally, the fluid was typically sampled at atmospheric pressure and temperature, but certain aspects of the present disclosure can sample the fluid under the actual high temperature and high pressure conditions experienced downhole, at the wellhead, or within the production pipeline system. In particular, for certain aspects, the fluid may remain in pressure communication with the wellbore so that the sample passing through the resonator is representative of the fluid passing through the wellbore.

With regard to the above resonant cavity design, the frequency setting on commercial EPR devices using this structure typically employs a mechanical tuning device. Certain aspects of the present disclosure operate autonomously, and thus, the tuning of the EPR device may be under processor control. Furthermore, a tuning screw would not be mechanically sound in the presence of the routine vibration seen on objects attached to wellheads and pipelines. For certain aspects of the present disclosure, there are no moving components to accomplish inductive coupling to the cavity or to accomplish resonance or near-resonance of the RF magnetic field.

Figure 3:
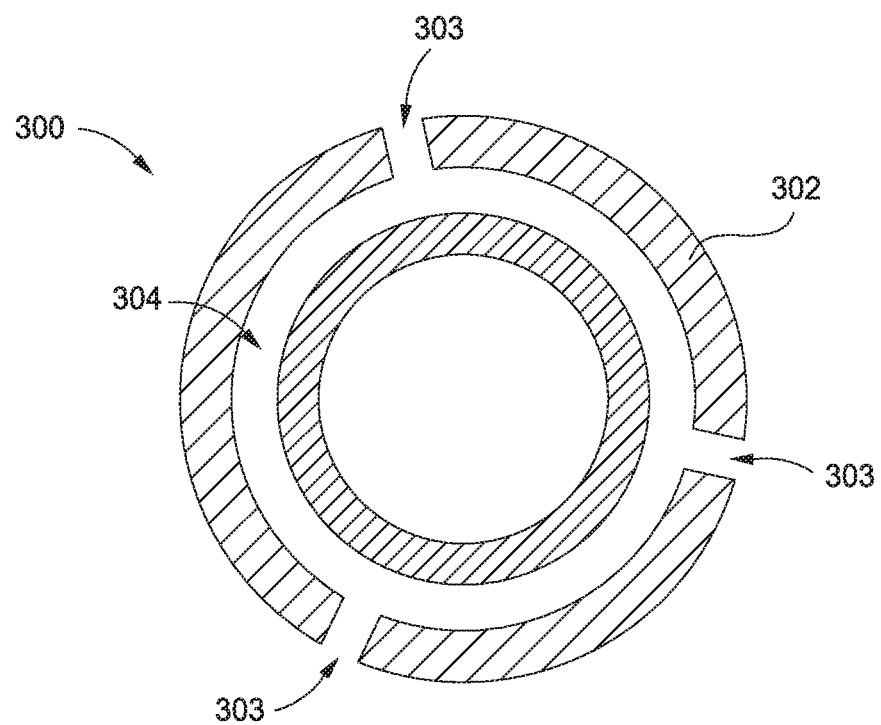
FIG. 3 is a cross-section of an example resonator containing a chamber, in accordance with certain aspects of the present disclosure.

These and other design considerations may lead to the example resonator 300 of FIG. 3, shown in cross-section, in accordance with certain aspects of the present disclosure. In the resonator 300, the sample (e.g., the oilfield fluid) may be contained in a tube 301, which may be a pressure-bearing chamber for withstanding the high temperatures and high pressures experienced downhole. The tube 301 may be made from polyether ether ketone (PEEK), with a possible manufacturer being Victrex PLC of Lancashire, United Kingdom (https://www.victrex.com/en/victrex-peek). PEEK is non-conducting, non-magnetic, and relatively transparent to electromagnetic (EM) waves in the GHz regime, so that PEEK can be incorporated within the structure of a loop-gap resonator. For certain aspects, the tube 301 may be a cylindrical container. The walls of the tube 301 may be surrounded by a housing 302. The housing 302 may also be cylindrical for certain aspects.

The cross-section shown in FIG. 3 is of the "gap" section of the resonator 300. In the gap section, the resonator 300 may have multiple gaps 303 in the housing 302 to concentrate the electric field in these gaps. Suitable performance may be obtained with 2 to 5 gaps, for example, although more or less than this range of gaps may be used. For example, S. Petryakov et al., "Single Loop—MultiGap Resonator for Whole Body EPR Imaging of Mice at 1.2 GHz," *Journal of Magnetic Resonance*, v188(1), pp. 68-73 (September 2007), describes the use of 16 gaps. The resonator 300 in FIG. 3 is depicted with three gaps 303. The housing 302 may be composed of any suitable electrically conductive material, such as metal. For certain aspects, copper (Cu) is used for the metal walls of the housing 302. To maximize sample area within the resonator 300, the metal walls of the housing 302 may be tightly bound onto the tube 301, minimizing the interface 304 therebetween.

Figure 4:
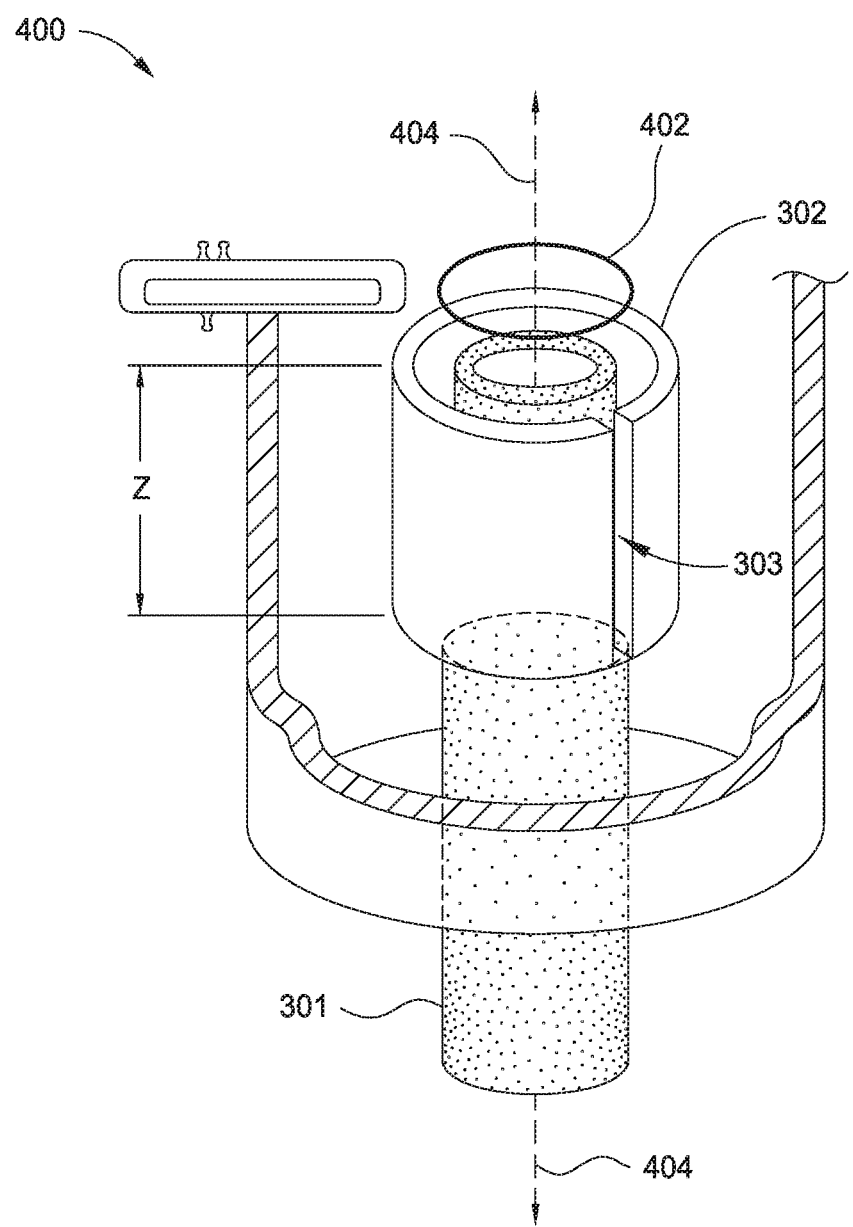
FIG. 4 is a cut-away view of an example loop-gap resonator with a chamber in the cavity, in accordance with certain aspects of the present disclosure.

To excite this resonator structure having a chamber in the cavity, a (circular) loop 402 (a coil) may be added to the flow system 400 above the gap section of FIG. 3, as shown in the cut-away view of FIG. 4, to form a loop-gap resonator. The tube 301 may be formed as a cylindrical chamber, with the loop 402 perpendicular to the longitudinal axis 404 of the cylinder. Although the loop 402 is illustrated as being circular in FIG. 4, the loop may have other suitable shapes, such as elliptical or oval. These shapes may depend on the cross-sectional shape of the housing 302. The loop-gap resonator of FIG. 4 may be constructed with a tight bond between the tube inlet, the housing 302, and the loop 402. This may provide structural integrity in order to survive vibration caused by the moving fluid. In one aspect, the height Z is about 1 inch (2.54 cm), and the inner diameter of the tube 301 is about ¼", which is a significantly higher diameter than is common in the EPR industry.

It is noted that other resonator designs are well known in the industry. U.S. Patent Application Publication No. 2015/0185299 to Rinard et al., entitled "Crossed-Loop Resonators" and filed Jan. 12, 2015, for example, discloses a crossed-loop resonator (CLR) that could also be applicable. The crossed-loop resonator uses two orthogonal lumped-element resonators—one to excite the spins and one to detect the electron paramagnetic resonance—to isolate the signal from the microwave source. Therefore, an EPR system implemented with a CLR may not include a circulator. As noted by Rinard, the high isolation provided by the CLR reduces the energy stored in the resonator that detects the signal, thereby reducing the intensity of the resonator ring down after the pulse, which decreases the instrument dead time. Another alternative design using surface-coil type resonators is given by H. Yokoyama and T. Yoshimura, "Combining a magnetic field modulation coil with a surface-coil-type EPR resonator," *Applied Magnetic Resonance*, Vol. 35, Issue 1, p. 127-135 (November 2008). A bimodal resonator has been described in Sundramoorthy et al., "Orthogonal Resonators for Pulse In Vivo Electron Paramagnetic Imaging at 250 MHz," *Journal Magnetic Resonance*, Vol. 240, pp. 45-51 (March 2014). The bimodal resonator achieves a 19 mm internal diameter with improved $B_1$ homogeneity compared to a loop-gap resonator of the same size and volume. The entire contents of these three documents are herein incorporated by reference.

Figure 5:
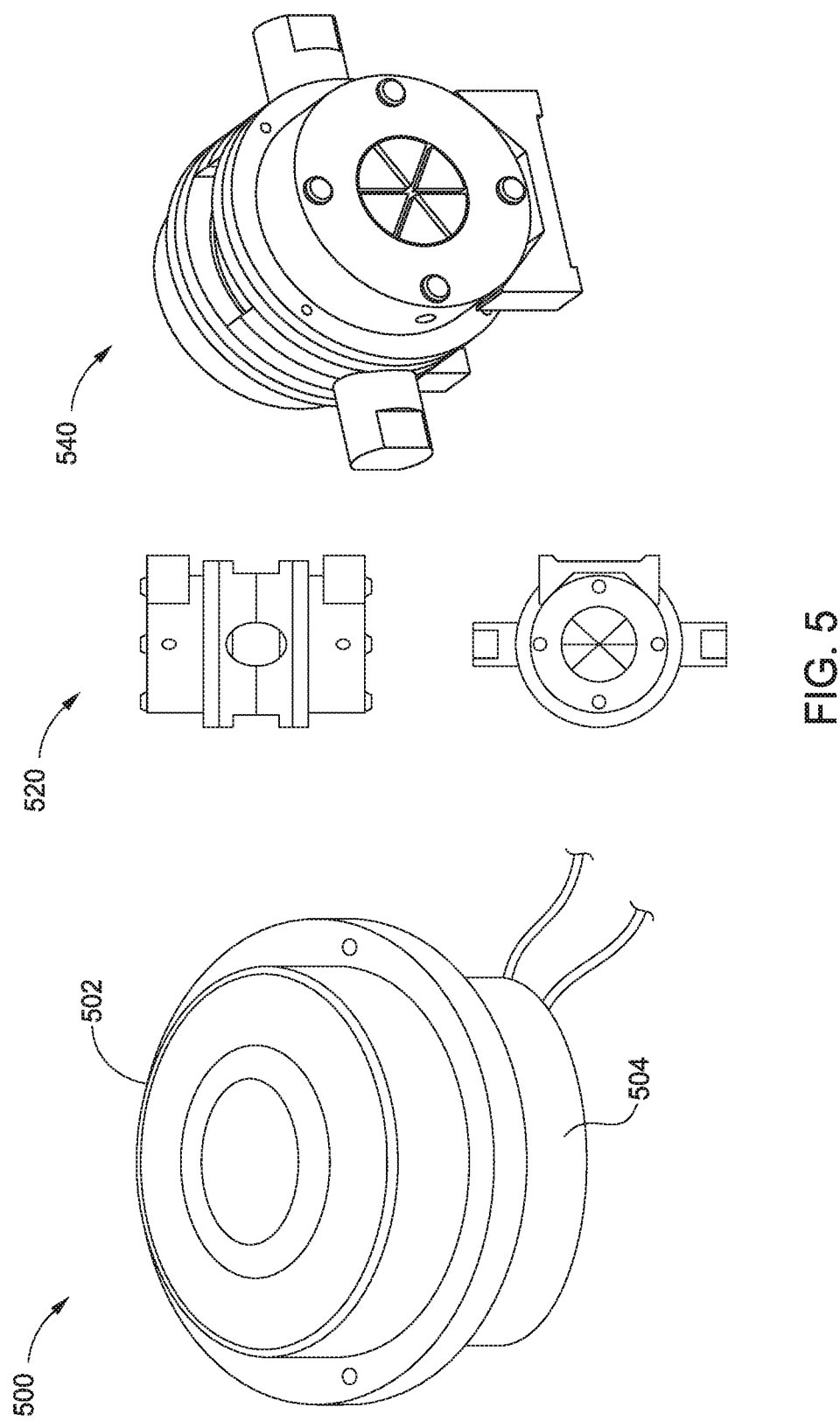
FIG. 5 illustrates an example electromagnet configuration for EPR, in accordance with certain aspects of the present disclosure.

As described above, static magnetic excitation for EPR can be performed with an electromagnet. FIG. 5 illustrates an example electromagnet 500, which may be implemented in certain aspects of the present disclosure. FIG. 5 also includes two-dimensional (2-D) computer-aided design (CAD) drawings 520 and a three-dimensional (3-D) CAD rendering 540 for the electromagnet 500. One electromagnet 500 may be positioned on either side of the sample tube (e.g., tube 301). Each electromagnet 500 may have 650-750 turns of 18 AWG magnet wire, for example. The magnet wire may be wound to form a coil 502 with high temperature epoxy and a 0.005" fiber glass tape used for insulation between turns. The entire assembly is rigidly housed in a non-magnetic housing 504. In an electromagnet, increasing the voltage on the coil increases the strength of the magnet (i.e., the magnetic flux density), which thereby enables a magnetic sweep.

Other magnetic configurations may be appropriate in some circumstances. As noted by Bales '303, for example, a further permanent magnet can be added to reduce the range specified for the magnetic sweep. Such a permanent magnet helps decrease the size of the electromagnet specified and so helps reduce the overall size and weight of an EPR system. The magnetic excitation of the electron spins may be accomplished with the combination of a static DC magnetic field generated by an electromagnet whose magnitude can be swept and an additional coil used to add a modulation frequency (e.g., a lower frequency modulation, such as in the audio frequency range) to that magnetic field.

Rather than determining the response to a particular magnetization directly, the DC magnet may be modulated with an additional small, low frequency (e.g., 100 kHz) coil of an electromagnet that creates a largely uniform magnetic field pointed in the same direction as the DC magnetic field $B_0$. For certain aspects, the coil 602 may be created by printing a circuit (e.g., metal traces) onto a multi-layer flexible printed circuit board (PCB) 600 as shown in FIG. 6 and illustrated in the conceptual diagram of a flow system 620. In the flow system 620, the flexible PCB 600 may be wrapped over the exterior of the (loop-gap) resonator 622 for certain aspects. The flexible circuit can be printed so that when folded in place, the flexible circuit creates two loops of a Helmholtz coil. Alternatively, as in the example of FIG. 6, the flexible PCB 600 can be folded to create two line sources, one on either side of the cavity. The magnetic field produced by the flexible PCB 600 is largely uniform over the fluid sample and in the same direction as that produced by the large electromagnets.

The design of the EPR system according to certain aspects of the present disclosure allows the sensitive electronics to be located away from the fluid sample to be probed and provides for significantly more efficient systems, such as co-placement of high-frequency components onto a single chip. A resonator (e.g., a loop-gap resonator) may appear as an inductive load on a microwave feed line, so the resonator may most likely be impedance matched with a coupling component, such as a varactor, similar to that described by Bales '303.

It is worth noting that the spectroscope need not operate at exactly the resonance frequency, but the closer the operating frequency is to resonance, then the larger the RF magnetic field induced and so the larger the EPR signal. To avoid dramatic dependence on getting an exact resonant frequency, the EPR spectroscope may have a cavity with a quality factor (Q) that is modestly high (e.g., >50), but not extremely high (e.g., >1000).

Figure 7:
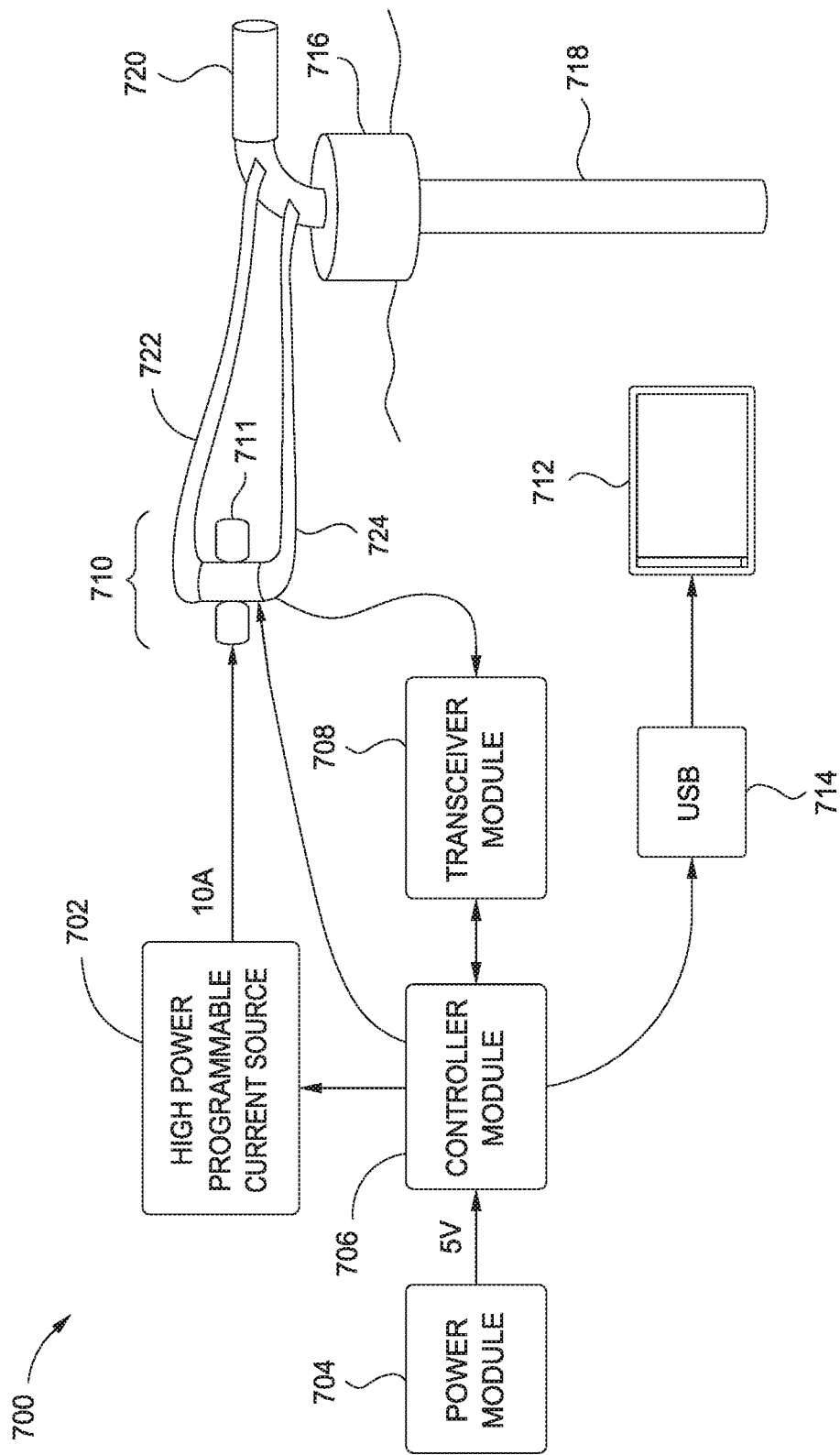
FIG. 7 is a block diagram of an example EPR system at a wellsite, in accordance with certain aspects of the present disclosure.

FIG. 7 is a block diagram of an example EPR system 700, in accordance with certain aspects of the present disclosure. As shown, the EPR system 700 comprises five modules: a high power programmable current source 702, a power module 704, a controller module 706, a transceiver module 708, and a resonator assembly 710. The high power programmable current source 702 may be implemented by a power supply with, for example, a gain of 5 A/V capable of 10 A with a 100 mH load. For certain aspects, an appropriate level of accuracy is 0.1% (±0.01 A). The output of this programmable current source 702 feeds a magnet 711 in the resonator assembly 710 to control the magnetic field. The controller module 706 may be capable of outputting a control voltage (e.g., ranging from 0 V to 2 V) to control the programmable current source 702. The power module 704 is a system capable of transforming mains electricity (e.g., 120 VAC at 60 Hz) to one or more DC voltages (e.g., 12 VDC, 5 VDC, and/or 5.5 VDC) for use in the EPR system 700. The transceiver module 708 is an EPR frequency board, capable of generating an RF signal for a resonator in the resonator assembly 710. Two board options may be considered for the transceiver module: an integrated circuit (IC) transceiver board and a discrete component transceiver board. For example, the discrete component transceiver board may use a 12 VDC power supply voltage output by the power module 704. Alternatively, the IC transceiver board may use a 5 VDC power supply voltage, which may be buffered through the controller module 706.

The EPR system 700 may also include a computer 712 or any of various other devices with a suitable processing system (e.g., a tablet, a smartphone, and the like). The computer 712 is capable of sending commands to and receiving data from the controller module 706 (e.g., via a USB/UART bridge 714).

As shown in FIG. 7, the EPR system 700 may remain in continuous fluid communication with equipment at a wellsite, such as a wellhead 716 disposed at the surface and/or production tubing 718 disposed in a wellbore. The production tubing 718 may be one of multiple tubulars in the wellbore. It is not uncommon, for example, that the production tubing 718 is contained within a number of strings of casing (not shown). The wellhead 716 as drawn figuratively represents the connection between a surface production pipeline 720 and the production tubing 718. As is well known in the industry, wellheads typically have a number of sample ports thereon, which allows an operator access to the fluid flowing from a reservoir. During production, the flow path from the production tubing 718 through the wellhead 716 to the pipeline 720 is generally maintained as a pressure barrier to disallow reservoir fluids from polluting the air and ground nearby. Consequentially, the fluid communication channels 722, 724 from the wellhead 716 to the resonator assembly 710 and back should be able to withstand internal fluid pressure. The connections of the channels 722, 724 to the wellhead 716 may be permanently welded or may be hose connections that are certified for exposure to oilfield fluids and pressures.

As drawn, the fluid connection for the channels 722, 724 is made downstream of the wellhead 716 and upstream of the surface pipeline 720, but other configurations may be utilized, which will be clear to those skilled in the art. For example, the connections may be located further downstream, such as in the vicinity of a pipeline manifold or at sample points along a pipeline as the pipeline transfers fluid from the wellbore to a refinery or vessel. Alternatively, the connections may be below the wellhead 716, such as in a scenario where the resonator assembly 710 is incorporated as an in-well sensor.

The computer 712 may be some significant distance away from the wellhead. In this case, the computer 712 may be in communication with the wellsite equipment by means of the cloud or other communications network. Indeed, in a typical oilfield setting, some components may need to be positioned close to the wellbore, while others may need to be located relatively far away. RF components, such as the resonator and the transceiver should be typically spaced within a few feet of each other, and to keep the channels 722, 724 short, the resonator may most likely also be positioned within a few feet of the wellhead. This means that these RF components may most likely be enclosed in one or more explosion-proof housings to avoid any safety issues, should there be accidental release of hydrocarbon at the wellhead. The power supplies, audio-frequency devices, etc. can be some distance removed from the wellhead without issue, so these components need not be in explosion-proof housing(s), but might benefit from being in housings to provide insulation from the rain, snow, heat, etc.

Figure 8:
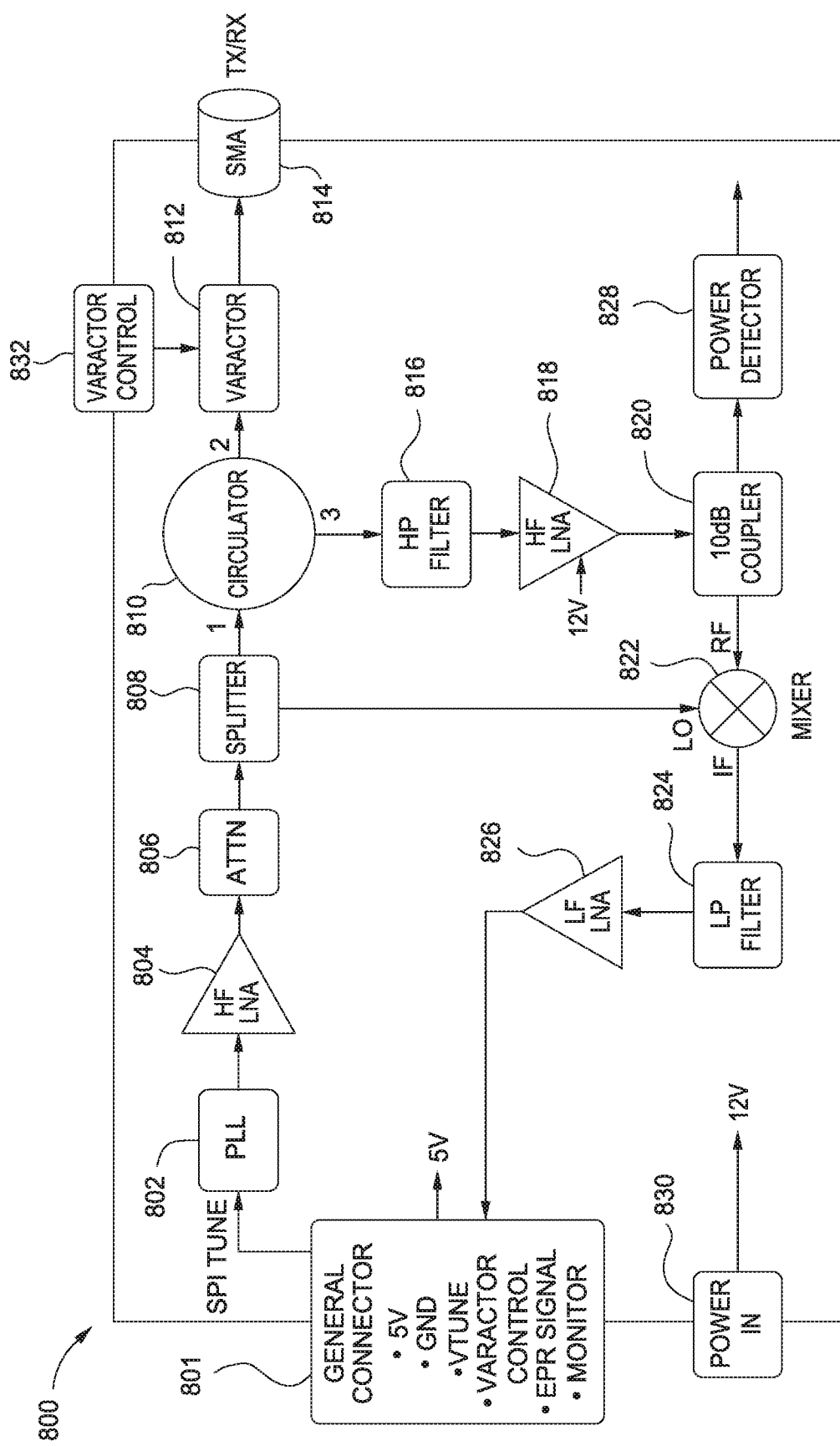
FIG. 8 is a block diagram of an example transceiver for an EPR system, in accordance with certain aspects of the present disclosure.

FIG. 8 is a block diagram of an example transceiver 800 for an EPR system, in accordance with certain aspects of the present disclosure. For example, the transceiver 800 may be implemented in the transceiver module 708 of FIG. 7. The transceiver 800 may include a transmit chain that includes a frequency synthesizer 802 (e.g., a PLL), an amplifier 804 (e.g., a high frequency (HF) low noise amplifier (LNA)), an attenuator 806, and a splitter 808 for generating a radio frequency (RF) signal for activating an RF field in the resonator cavity. To couple the RF signal to the resonator, the transceiver 800 may also include a circulator 810, an impedance matching circuit 812 (comprising, e.g., a varactor), and a connector 814 (e.g., an SMA coaxial connector). The transceiver 800 may also include a receive chain that includes a filter 816 (e.g., a high pass filter or a bandpass filter), an amplifier 818 (e.g., an HF LNA), a coupler 820 (e.g., a 10 dB coupler), a mixer 822, a filter 824 (e.g., a low-pass filter), and an amplifier 826 (e.g., a low frequency (LF) LNA). The transceiver 800 may also include a power detector 828.

As described above, the purpose of the impedance matching circuit 812 is to make the combined impedance of this circuit and the resonator match that of the effective impedance looking back into the transmit path for a particular frequency or range of frequencies. The resonator may typically appear as a mostly inductive load, so the impedance matching circuit 812 may be designed to have a capacitive component. The impedance matching circuit 812 may therefore vary the capacitance(s) of the capacitive element(s) to effectively adjust the impedance in an effort to minimize reflections. It will be apparent to those skilled in the art that this matching technique may be referred to as "an impedance sweep to set the impedance of an impedance matching circuit associated with the generation of the RF magnetic field." The value chosen for that impedance (or, more specifically in some cases, the capacitance) will vary according to the electromagnetic properties of the fluid in the cavity.

For one aspect, the following is a list of the key components for the different blocks of the transceiver 800:
    frequency synthesizer 802: HMC837 Evaluation Board (http://www.analog.com/en/products/rf-microwave/pll-synth/fractional-n-plls/hmc837.html);
    circulator 810: DITOM D3C4450 (https://www.ditom.com/images/D3C4450.pdf);
    splitter 808: RF-Lambda RFLT2W2G08G (http://www.r-flambda.com/pdf/medpowercombinersplitter/RFLT2W2G08G.pdf)
    attenuator 806: Mini-Circuits VAT-3+(http://www.mini-circuits.com/pdfs/VAT-3+.pdf);

amplifier 804 or 818 (e.g., a HF LNA): RF-Lambda RLNA01M06GE (http://www.rflambda.com/pdf/lowno seamplifier/RLNA01M06GE.pdf);

coupler 820: Mini-Circuits ZUDC10-183+(https://www.minicircuits.com/pdfs/ZUDC10-183+.pdf);

power detector 828: RF Bay RPD 5501 (http://rfbayinc.com/products_pdf/product_445.pdf);

filter 816 (HP filter: Mini-Circuits VHF-3100+(https://www.minicircuits.com/pdfs/VHF-3100+.pdf);

filter 824 (LP filter): Mini-Circuits SLP-1.9+(http://www.minicircuits.com/pdfs/SLP-1.9.pdf);

amplifier 826 (LF LNA): RF Bay LNA 1800 (http://rfbayinc.com/products_pdf/product_94.pdf);

mixer 822: Fairview MW SFM2018 (https://www.fairviewmicrowave.com/images/productPDF/SFM2018.pdf);

impedance matching network 812 (e.g., a varactor board): DAC LTC2615 (http://www.linear.com/product/LTC2615); and connector 814 (SMA): (https://cinchconnectivity.com/OA_MEDIA/specs/pi-142-0701-801.pdf).

Additional components may be added to the circuit shown in FIG. 8. For example, in certain aspects, one or more filters may be added to the circuit. One non-limiting example of a filter includes a DC blocking filter (e.g., a high-pass filter or a bandpass filter), which may be connected in series with the impedance matching network 812 (e.g., with the variable capacitor). The impedance control signal (e.g., output by the controller module 706 and connected to the transceiver 800 via a connector 832) may be an analog control signal or a digital control signal (e.g., for a switched capacitor). When this combination is used, extremely fast feedback is possible. Note that the PLL HMC767 has a settling time of 433 µs and the DAC LTC2615 has a settling time of just 7 µs. Yet, still faster operation is possible as will be clear to those skilled in the art.

With the recent advancement in fast-settling PLL frequency synthesizer technologies, it is possible to change the frequency of the local oscillator (LO) 834 in the EPR system in a few microseconds. For example, Analog Devices ADF4193 is a low phase noise, fast settling PLL frequency synthesizer available from Analog Devices, Inc. of Norwood, Mass. The ADF4193 provides frequency hopping in 5 µs and phase settling by 20 µs. The following is a hyperlink to the datasheet for the ADF4193: http://datasheet.octopart.com/ADF4193BCPZ-Analog-Devices-datasheet-10548259.pdf.

Furthermore, with the advancement of digital-to-analog converter (DAC) technologies and drivers for capacitive loads, it is possible to change the value of the varactor(s) used in the matching network in timescales on the order of 10 ns. For example, Texas Instruments DAC39J84 is a quad-channel, 16-bit, 2.8 giga-samples per second (Gsps) interpolating DAC available from Texas Instruments Inc. of Dallas, Tex. The DAC39J84 provides sample rates exceeding 1 GHz that can be used to drive a varactor. The following is a hyperlink to the datasheet for the DAC39J84: http://www.ti.com/product/DAC39J84/datasheet/abstract#SLASE1644.

Although the DAC can operate in timescales shorter than 1 ns, the settling time of the impedance matching network 812 may be fundamentally limited by the quality factor (Q) of the matching network. For example, for a resonance frequency of 5 GHz and Q of 100, the settling time may be limited to 200 µs×100=20 ns.

For certain aspects, the EPR system may also measure the magnetic field inside the cavity through the addition of a Hall effect sensor, or equivalent, as disclosed, for example, by U.S. Patent Application Publication No. 2015/0185255 to Eaton et al., entitled "Hall Probe, EPR Coil Driver and EPR Rapid Scan Deconvolution" and filed Feb. 5, 2015, the entire contents of which are herein incorporated by reference. The output of the EPR spectrum can be scaled by this measured magnetic field value to allow estimation of the number of electron spins per unit volume ("Ng" in the terminology of EPR spectral analysis).

Figure 9:
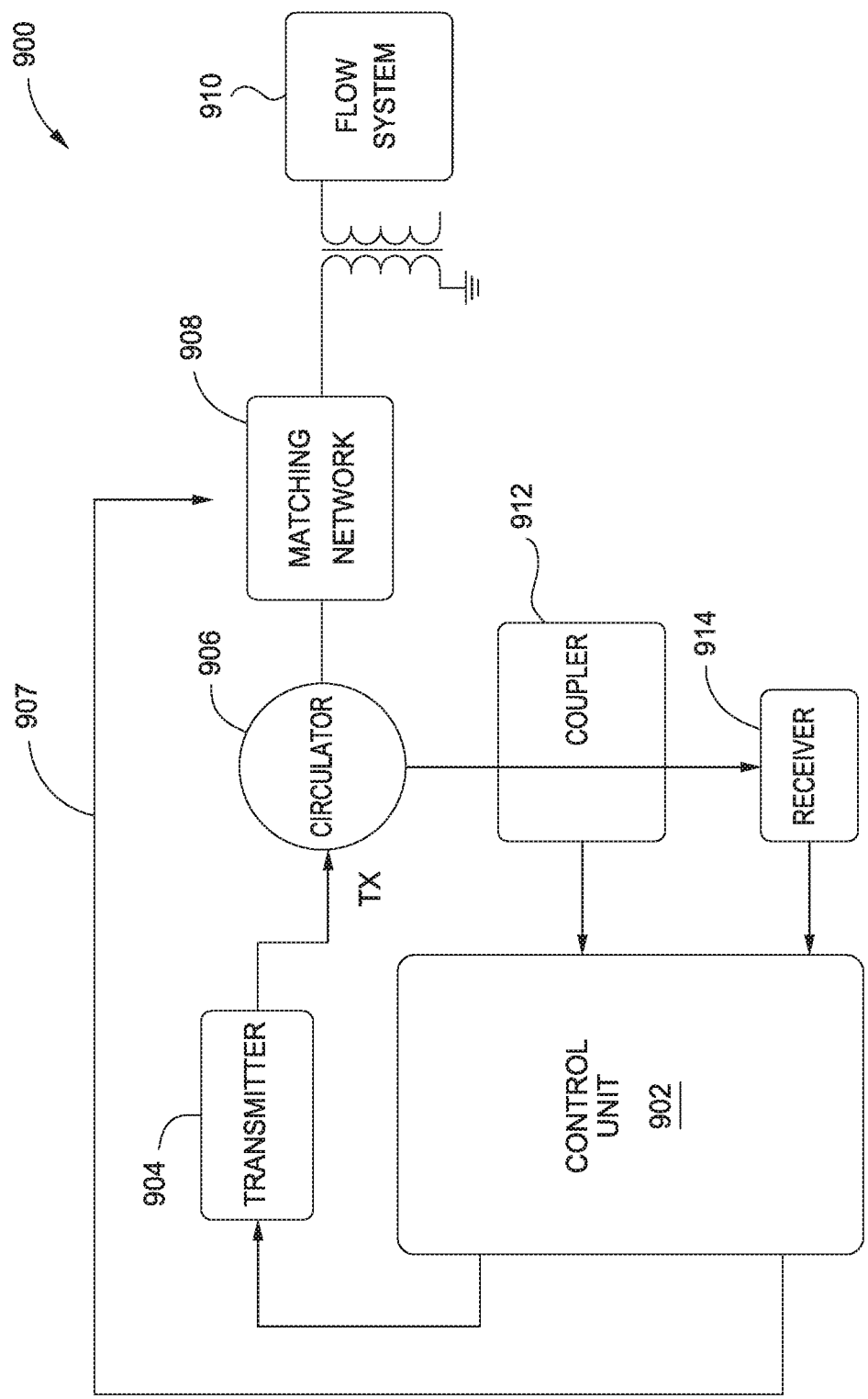
FIG. 9 is a block diagram of an example EPR system illustrating feedback loops for impedance and frequency adjustment, in accordance with certain aspects of the present disclosure.

Considering these improvements as part of the EPR system 900, as shown in FIG. 9, the overall feedback process can be done very fast, allowing the network to adjust in real-time to changes in the flowing fluid. The flow system 910 has an impedance that is a function of the resonator design, the materials used in the resonator, and the properties of the fluid flowing therethrough. Thus, the flow system 910 may changes its impedance continuously while the fluid is flowing, especially in the case of multiphase fluid from hydrocarbon recovery operations. Therefore, to achieve maximum transfer of energy and low power reflection, the impedance matching network 908 should adjust its impedance to make a match between the effective impedance looking back into the transmit path and the combined impedance of the matching network 908 and the resonator surrounding the sample chamber in the flow system 910.

As noted above, the network 908 is capable of modifying its impedance by means of a programmable matching network in series with the transmission line. Non-limiting examples of the programmable capacitance include a varactor or a switched capacitor. In the case of a varactor, a DC voltage controls the capacitance of the varactor. A feedback loop reads the reflected signal via a directional coupler 912. Non-limiting examples of the directional coupler 912 would be a 20 dB coupler, a 10 dB coupler, a 3 dB coupler, etc. A system with a smaller coupling is desired because smaller coupling results in a smaller loss in the main EPR signal, which results in a higher EPR power to the input of the EPR receiver 914. Although the coupler 912 passes the desired EPR signal to the receiver, the coupler is also used to measure the amount of the undesired reflected signal from the resonator. A smaller reflected signal means that more power can be sent to the resonator by the transmitter 904 without causing saturation of the receiver 914 by the reflected signal. The reflected power coming out of the coupler 912 may be measured to tune the impedance of the matching network 908 (e.g., the capacitance of the variable capacitor(s)) and hence maintain desired matching.

Since different flow types have different dielectric constants and conductivities, the power of the reflected signal can be periodically measured to determine the impedance of the resonator and its matching quality. The reflected signal from the coupler 912 may be converted to a DC voltage using a power detector (not shown). This DC voltage then can be digitized using an analog-to-digital convertor (ADC) (not shown) and fed into the control unit 902. The control unit 902 may be composed of at least one microprocessor, microcontroller, programmable integrated circuit (e.g., a field-programmable gate array (FPGA)), or application-specific integrated circuit (ASIC). The control unit 902 may use an algorithm to generate the control signal 907 to change the impedance of the matching network 908 (e.g., an actuation signal to change the value of the tunable capacitor), in an effort to match this impedance to the impedance of the resonator in the flow system 910.

It is to be understood that the impedance matching network 908 may include multiple capacitors in parallel and/or in series, some of which may be variable, while others may be fixed. These capacitors (fixed and/or variable) may also have switches connected in series or in parallel therewith for effectively enabling and disabling various capacitors in an effort to adjust the overall capacitance of the impedance matching network 908. A person having ordinary skill in the art will understand that the overall impedance matching network 908 may effectively have a variable capacitance that can be adjusted (e.g., by a control signal 907 output from the control unit 902).

In addition to changing the impedance of the matching network 908, the control unit 902 may adjust the frequency of the transmitter 904 to achieve a substantial value of the reflected signal. As a non-limiting example, the mechanism for changing the impedance of the matching network 908 or the frequency of the transmitter 904 may be accomplished by using one or more digital-to-analog converters (DACs) inside or external to the control unit 902. In this case, a DAC may receive a digital signal from the control unit 902, generate an analog signal (e.g., control signal 907), and control the impedance of the matching network 908 (e.g., the variable capacitance of a varactor). In this case another DAC may be used to control the frequency of the transmitter 904 by adjusting the tuning voltage of a voltage-controlled oscillator (VCO). Alternatively, the control unit may send a digital control signal to a programmable phase-locked loop (PLL) to set the frequency of the transmitter 904.

Circuitry can be included to automatically set the transmitter frequency to the resonant frequency of the resonator cavity. This need not be the optimal strategy, however. For example, to obtain the most stable frequency, it can be advantageous to have a frequency synthesizer (e.g., in the transmitter 904) that operates at discrete intervals, so that the synthesizer can get to the discrete frequency interval (e.g., 100 kHz) at or closest to the resonant frequency. In this case, the cavity may not be fully excited to resonance, but one can be confident that there would be extremely minimal phase noise and jitter in the value of that frequency. It has been noted earlier that it is not the resonance condition which creates an EPR signal; rather, the key is having a sufficiently large RF magnetic field perpendicular to the DC magnetic field.

For certain aspects, a circuit could be automatically locked to the closest discrete frequency step (e.g., 100 kHz) with no additional information being recorded. For other aspects, however, the RF frequency may first be swept, and the reflected signal may be measured, to yield a graph for the cavity response, similar to the graph 1000 of FIG. 10.

Figure 10:
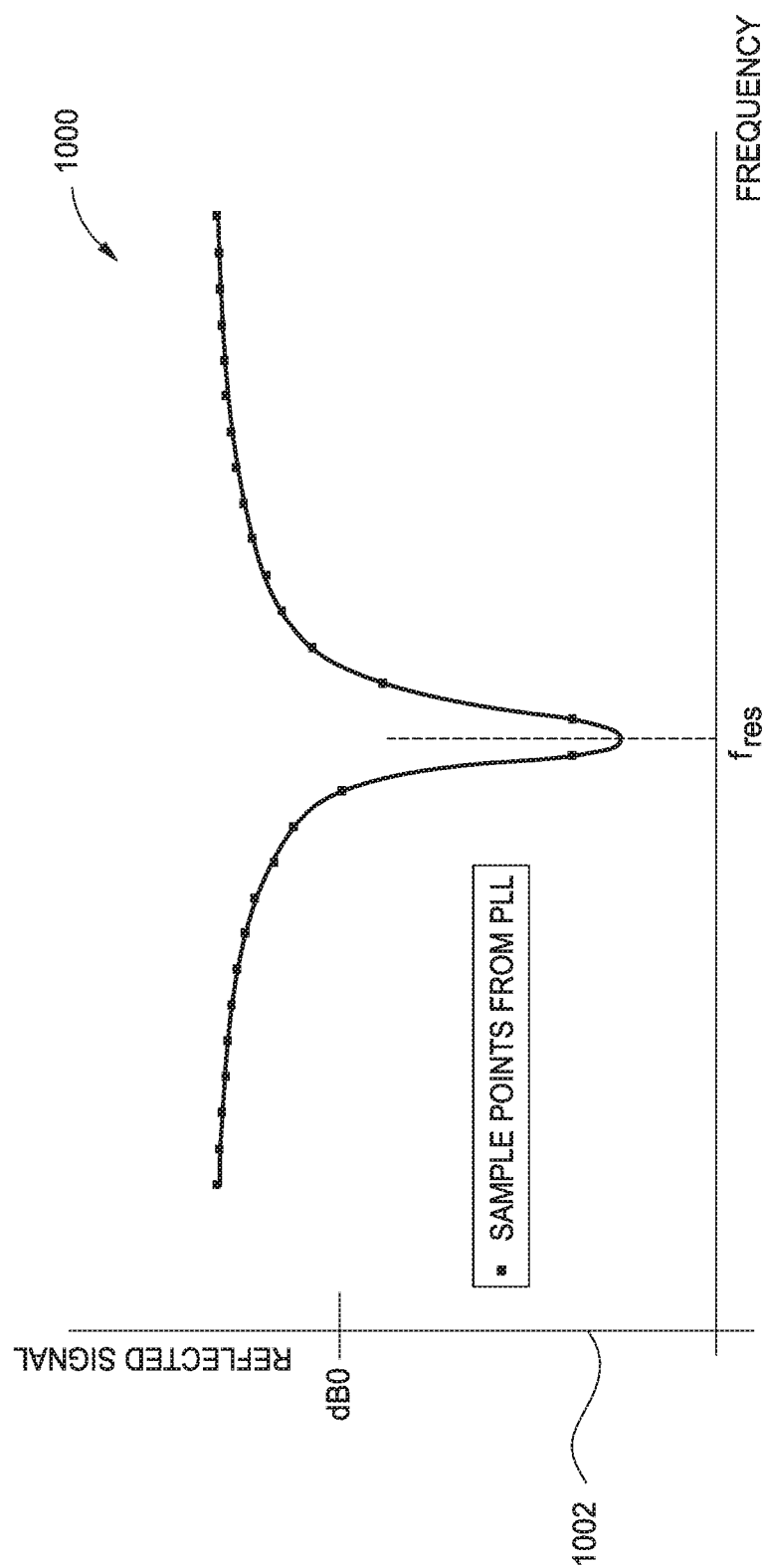
FIG. 10 is an example graph illustrating reflected signal parameters from a sweep of discrete frequencies and identification of a resonance point, in accordance with certain aspects of the present disclosure.

In FIG. 10, the axis 1002 for the reflected signal can represent the reflected total amplitude or the reflected in-phase contribution (voltage or power). The frequency steps may be set by the frequency synthesizer (e.g., implemented by a phase-locked-loop (PLL) or VCO) in the EPR system. The condition dB0 represents a preset value known to give an acceptable response of the EPR machine: any value of frequency with reflection signal less than dB0 will provide enough RF magnetic field strength to create a measurable EPR response. It can be seen that the discrete frequency with the lowest reflected signal is not exactly equal to the resonant frequency. Moreover, when comparing data from one magnetic sweep to another, if the fluids have not changed, it is advantageous to be using the same discrete frequency; otherwise, this can create an artificial offset between the two EPR responses.

This leads to the following search strategy: sweep over a given range of frequencies, then for those frequencies giving a signal less than dB0, choose that frequency which is equal or closest to the previous frequency used. This technique has been found to give very stable EPR response as fluids flow through the cavity. This technique also avoids the possibility of an automated frequency control loop locking into an erroneous value (as has been cited as a problem by Hyde '554, for example).

There remains a further improvement that can be made. It is known that complex permittivity data can be derived through measurements of the resonance frequency of a cavity (e.g., see "Measurement of Complex Permittivity and Permeability through a Cavity Perturbation Measurement," Master's Thesis in Applied Physics by Tomas Rydholm, Chalmers University of Technology, Sweden, 2015). For example, water (which typically has a dielectric constant near 80) reduces the resonant frequency of the resonator cavity compared to oil (which has a dielectric constant between 2 to 8). This is because the high dielectric constant of water increases the parasitic capacitance of the resonator and reduces its resonance frequency. In addition, the high conductivity of the flow (e.g., brine with high salinity) reduces the effective quality factor of the resonator. This is because the loss of the resonator cavity increases due to conductivity of the flow. Note that high conductivity will appear to the EPR sensor as an imaginary component to the dielectric, so that by solving for complex permittivity, one can obtain both "real" dielectric constant and fluid conductivity.

As noted, the algorithm described above for choosing the EPR frequency may not output the actual resonant frequency, but rather a frequency with a reflected signal parameter less than dB0. However, the theoretical response of the cavity can be readily modelled (e.g., Rydholm, op. cit.) for a particular (complex) dielectric value. A minimization algorithm such as Levenberg-Marquadt can then be used to find that (complex) dielectric value which gives the closest fit to all of the measured data. The modelling can take into account the known structure of the resonator (e.g., the dimensions of the sample chamber within the pressure housing, the materials for that pressure housing, etc.). The quality factor of the resonator may also be calculated from this data since the reflected signal parameter is measured as a function of the transmitter frequency (as in the graph 1000 of FIG. 10). This technique can be used to build an online flow impedance sensor.

Figure 11:
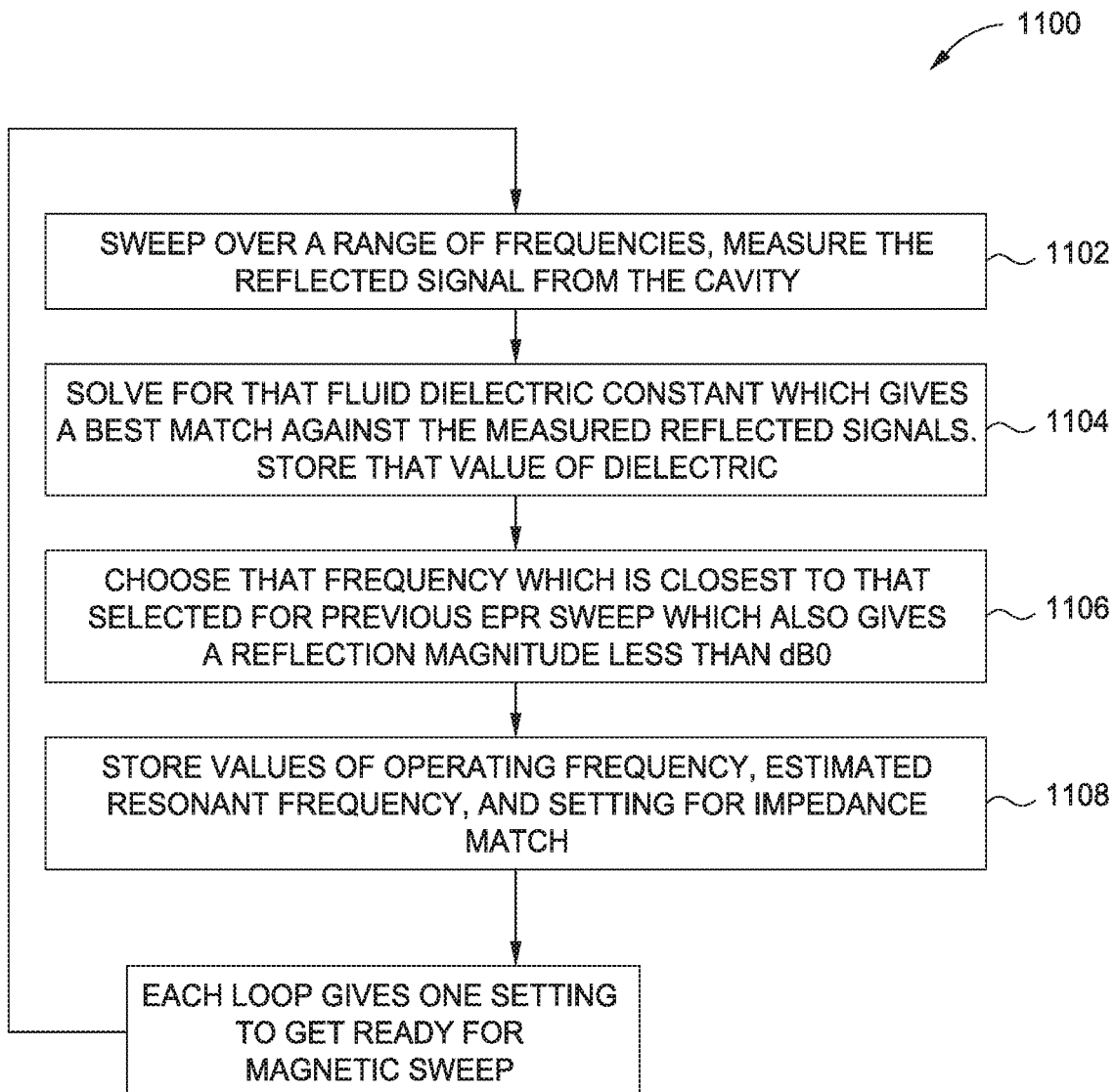
FIG. 11 is a flow diagram of example operations for determining both dielectric permittivity information and an impedance match, in accordance with certain aspects of the present disclosure.

FIG. 11 is a flow diagram of example operations 1100 for determining both dielectric permittivity information and an impedance match, according to the workflow described above. The operations 1100 may be performed, or at least controlled, by a control unit, such as the control unit 902 of FIG. 9.

The operations 1100 may begin, at block 1102, by sweeping over a range of frequencies for the RF magnetic field and measuring the reflected signals from the resonator cavity. At block 1104, the control unit may solve for the fluid dielectric constant that gives the best match to the measured reflected signals. The value of this solution may be stored in memory (not shown) of the EPR system, which may be connected to or part of the control unit. At block 1106, the control unit may choose a frequency that is at or closest to the frequency selected for a previous EPR sweep and that also gives a reflection parameter value (e.g., magnitude) that is less than a threshold value (e.g., dB0). At block 1108, the values of the operating frequency, the estimated resonant frequency, and the setting for the impedance match may be stored (e.g., in memory of the EPR system). The blocks 1102, 1104, 1106, and 1108 may be repeated, where each iteration through these blocks provides one setting of frequency and impedance before a DC magnetic sweep is performed. Alternatively, it is also possible to keep the same impedance and frequency but perform multiple sweeps of the DC magnetic field. This can be done, for example, to measure multiple EPR spectra, average these measured spectra, and thereby reduce the noise on the output EPR spectrum.

For other aspects, instead of determining the dielectric constant (or complex permittivity) directly, it would also be possible to compute the exact resonant frequency and quality factor for each frequency sweep and store these values.

With regard to the optimizations, or at least adjustments, of the impedance match and the frequency, these can be done sequentially or concurrently. Non-limiting examples for the optimization algorithms include gradient descent, quasi-newton, random search, or simulated annealing.

Different possibilities exist for the timing of the magnetic sweep. As noted above, for certain aspects in EPR logging, not only is a DC magnetic field created, but a small, low frequency modulation is added, where that modulation is done to create a magnetic field parallel to the DC magnetic field. This results in the workflow depicted in FIG. 12.

Figure 12:
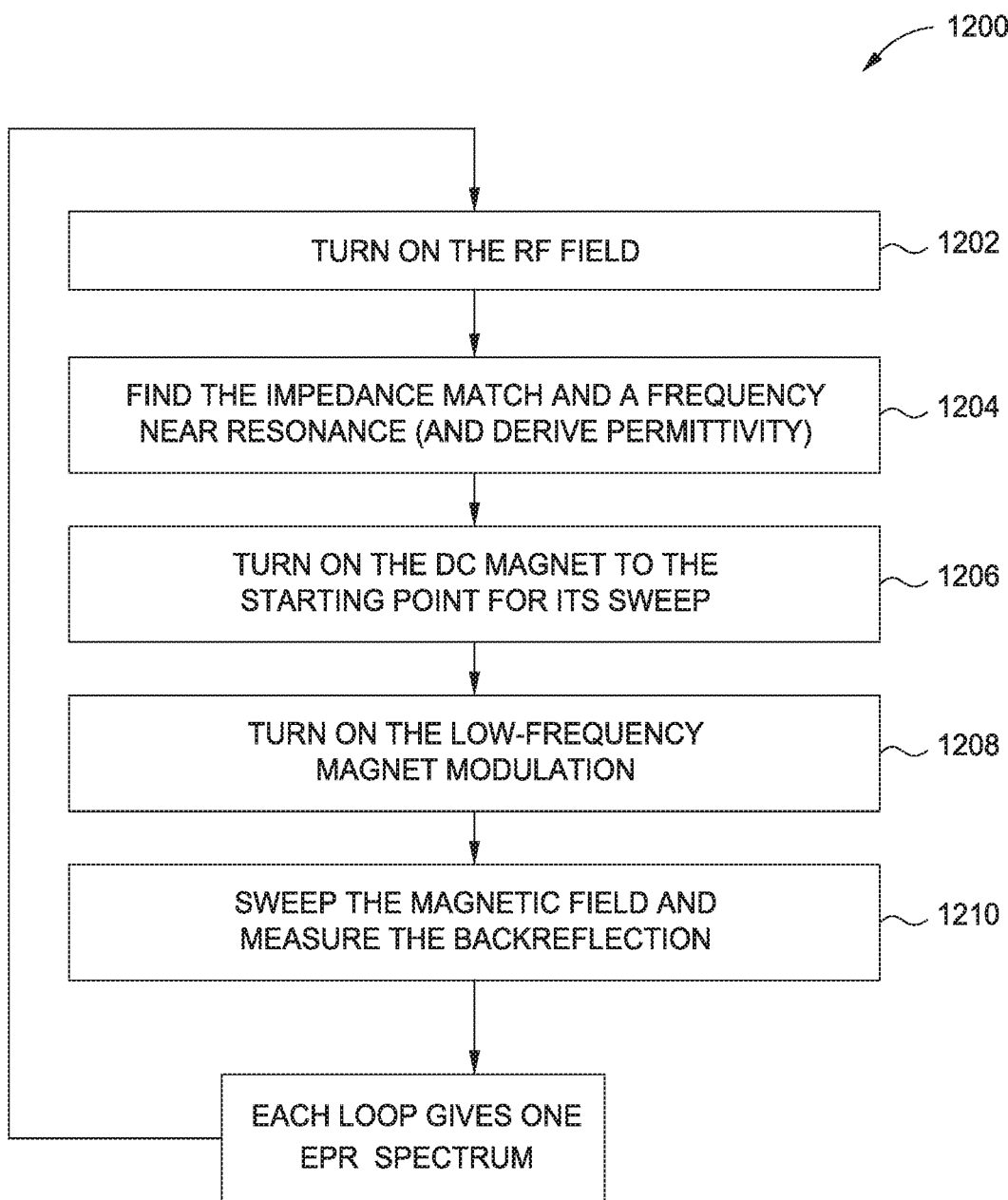
FIG. 12 is a flow diagram of example operations for deriving an EPR spectrum using low-frequency magnet modulation, in accordance with certain aspects of the present disclosure.

FIG. 12 is a flow diagram of example operations 1200 for deriving an EPR spectrum using low-frequency magnet modulation, in accordance with certain aspects of the present disclosure. The operations 1200 may be performed, or at least controlled, by a control unit, such as the control unit 902 of FIG. 9.

Figure 13A:
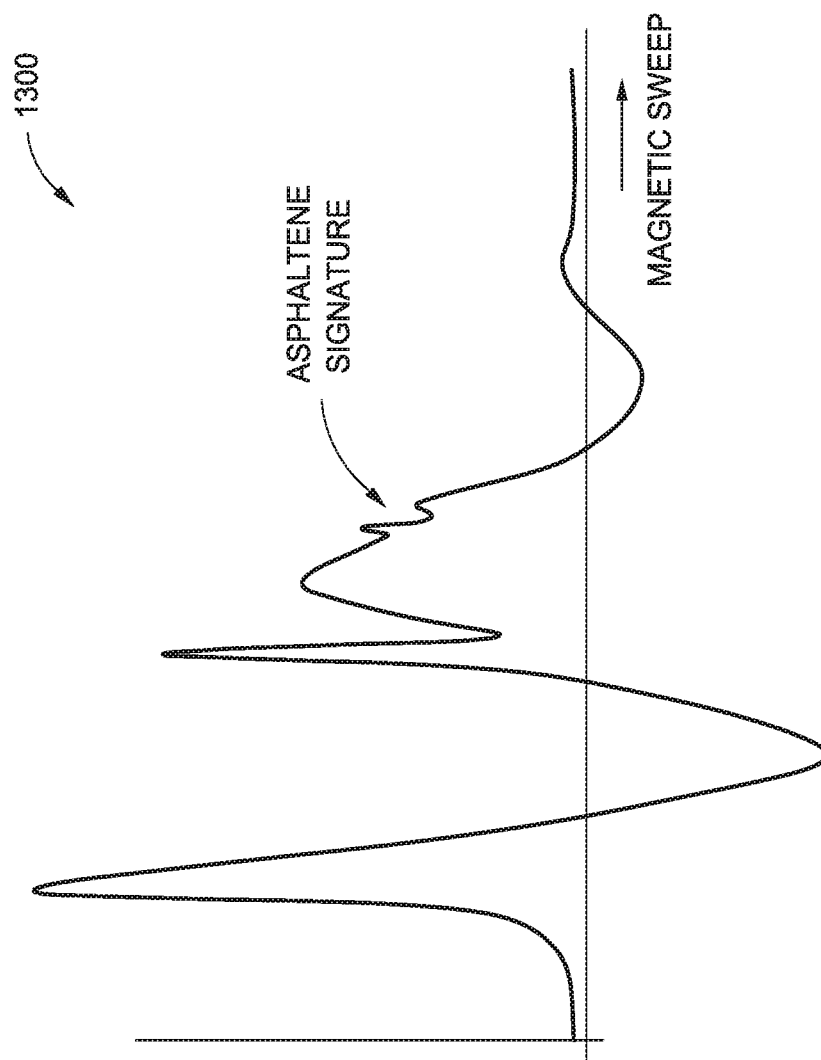
FIG. 13A is a graph of an example EPR response over a relatively larger magnetic sweep range, in accordance with certain aspects of the present disclosure.

The operations 1200 may begin, at block 1202, by turning on the RF field such that the RF field is applied to the resonator cavity. At block 1204, impedance matching may be performed, and a frequency at or near resonance may be found. For certain aspects, the control unit may also derive permittivity as described above. At block 1206, the control unit may turn on the DC magnet to the starting point of the magnetic sweep. The low-frequency magnet modulation may be turned on at block 1208. At block 1210, the magnetic field may be swept, and the reflected signals may be measured. The blocks 1202, 1204, 1206, 1208, and 1210 may be repeated, where each iteration through these blocks provides one EPR spectrum (e.g., as shown in FIG. 13A and described below).

In general, for asphaltene detection, the signal is much smaller than that of "background" components, such as metal ions in the fluid, so there is an interest in zeroing out the background signal to focus on the asphaltene measurements. For example, FIG. 13A is a graph 1300 illustrating an example full EPR response, which shows multiple peaks from different resonances. An illustration of an asphaltene signature is shown but, in reality, it may be significantly smaller than the surrounding peaks, as depicted in the graph 1300. FIG. 13A is a graph 1320 illustrating the same curve as FIG. 13A, but in the graph 1320, the DC magnetic field sweep is initiated only over the magnetic interval pertinent to an asphaltene measurement.

An overall EPR absorption curve would be the sum of individual Lorentzian or Gaussian components centered at particular magnetic field strengths, each having a line width dependent on the T1 and T2 relaxation values for that particular spin contribution. Because EPR spectrometers modulate the magnetic field, the output of the spectrometer does not look like the sum of such components, however, but is instead the derivative. Thus, the asphaltene signature becomes a "doublet," as illustrated in the graph 1320 of FIG. 13B.

In some scenarios, it may be desirable to sweep a full magnetic range (e.g., from 0 T to 0.2 T). This is the case, for example, when looking for the quantity of some metal ions that have a very broad line width. In other scenarios, it may make sense to sweep a narrower magnetic range. For example, at RF excitations in the 3-5 GHz range, it is known that the asphaltene response will occur in the magnetic flux density interval of 0.15 T to 0.17 T, so it is completely reasonable to only sweep that magnetic range (or a range slightly greater than that range). The values 0.15 T and 0.17 T are chosen to demonstrate the example and are not to be taken as limitations of the present disclosure. Also, as mentioned above, the Larmor frequency of an EPR component depends on the ratio of DC magnetic field to RF excitation frequency, so if, say, a 0.15 T to 0.17 T DC magnetic field sweep is chosen with an RF magnetic field near 4.5 GHz, then a 0.3 T to 0.34 T DC magnetic field sweep would be the appropriate range for an RF magnetic field near 9 GHz. As noted above, sweeping a narrower magnetic range can allow for a more rapid scan, which can be advantageous when fluids are rapidly flowing. As described above, a combination of a permanent magnet and an electromagnet may be used, so in this scenario, an EPR system may include a permanent magnet to provide a magnetic flux density of 0.15 T and a significantly smaller electromagnet to provide the additional range of 0 to 0.2 T. This would allow very rapid sweeping (less than 1 second), which may be appropriate for very fast-moving fluids (e.g., around 30 feet/s).

However, it is also clear from the above example that the EPR response at 0.15 T is nonzero. This means that there is a nonzero AC magnetic susceptibility as a result of that value of DC magnetic field. If the matching circuit had been set to give minimal impedance mismatch at zero field (0 T), then there will now be an impedance mismatch unrelated to the presence of asphaltene in the range of interest therefor. Consequently, instead of making a coupling match with the magnets turned off, a coupling match may be made for certain aspects with the magnet set to its initial sweep value for the paramagnetic material of interest (e.g., 0.15 T for asphaltene). This significantly increases the signal-to-noise ratio (SNR) for the measurement over the narrowed range.

Similarly, for certain aspects, a frequency may be chosen that resonates not an empty cavity, nor a simple fluid-filled cavity, but a frequency that gives minimal reflection when the fluid is undergoing whatever Zeeman effect the cavity experiences at the initial magnetic field sweep value.

It is also noted that while the Zeeman effect may change p in the presence of an applied magnetic field, the same is not true of the permittivity. Consequently, it is still of use to compute the dielectric and conductivity values from the reflection data at the initial sweep. This gives the workflow of FIG. 14.

Figure 14:
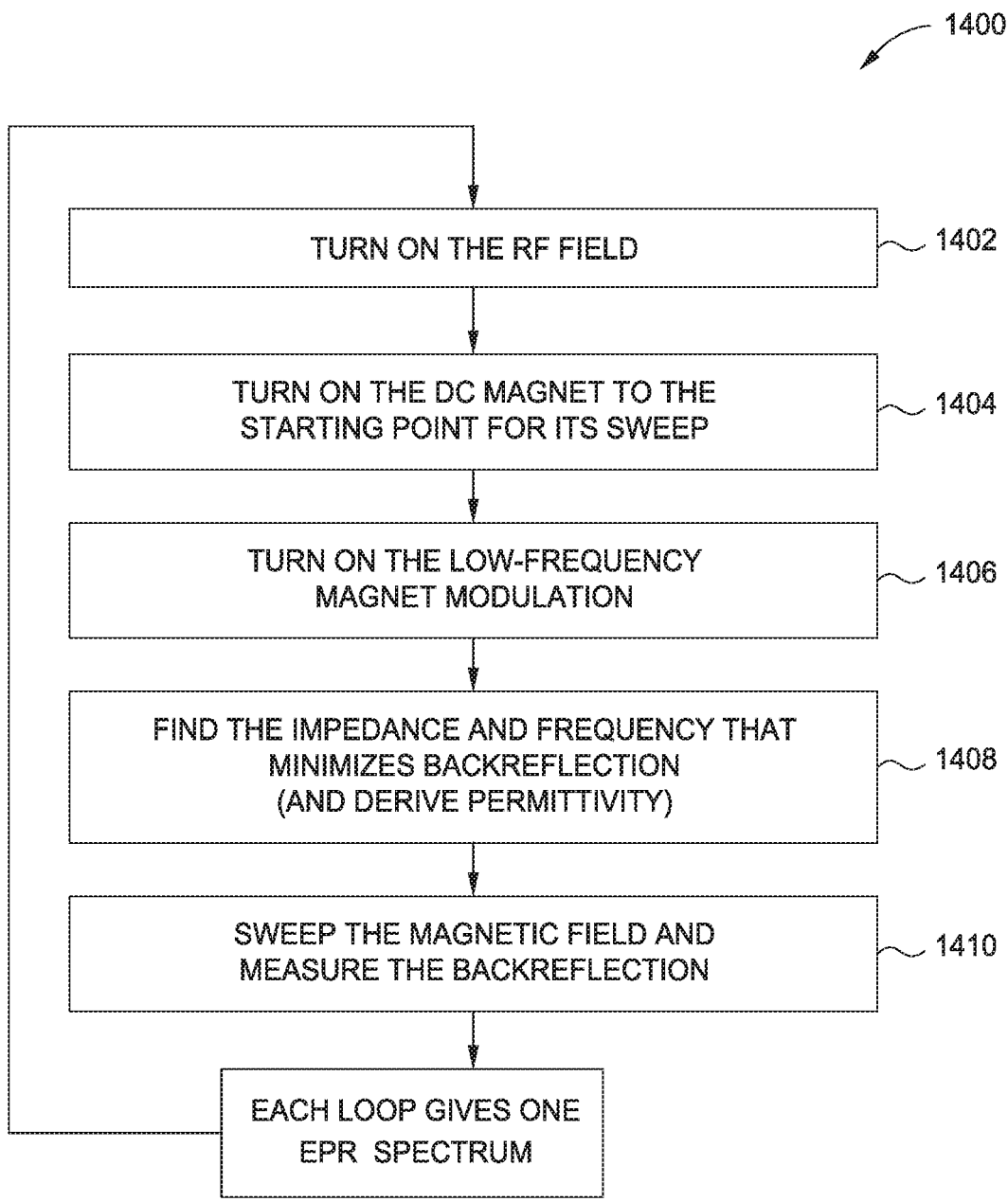
FIG. 14 is a flow diagram of example operations for deriving a local EPR spectrum by performing impedance and/or frequency sweeps with the DC magnet activated, in accordance with certain aspects of the present disclosure

FIG. 14 is a flow diagram of example operations 1400 for deriving a local EPR spectrum by performing impedance and/or frequency sweeps with the DC magnet activated, in accordance with certain aspects of the present disclosure. The operations 1400 may be performed, or at least controlled, by a control unit of an EPR system, such as the control unit 902 of FIG. 9.

The operations 1400 may begin, at block 1402, by turning on the RF field such that the RF field is applied to the resonator cavity. At block 1404, the control unit may turn on the DC magnet to the starting point of the magnetic sweep. The initial value for the magnetic sweep may be based on the magnetic range for the particular paramagnetic material of interest. The low-frequency magnet modulation may be turned on at block 1406. At block 1408, impedance matching may be performed, and a frequency at or near resonance may be found, both with the magnet activated. For certain aspects, the control unit may also derive permittivity as described above. At block 1410, the magnetic field may be swept, and the reflected signals may be measured. The blocks 1402, 1404, 1406, 1408, and 1410 may be repeated, where each iteration through these blocks provides one EPR spectrum (e.g., as shown in FIG. 13B for the narrowed magnetic sweep).

Figure 15:
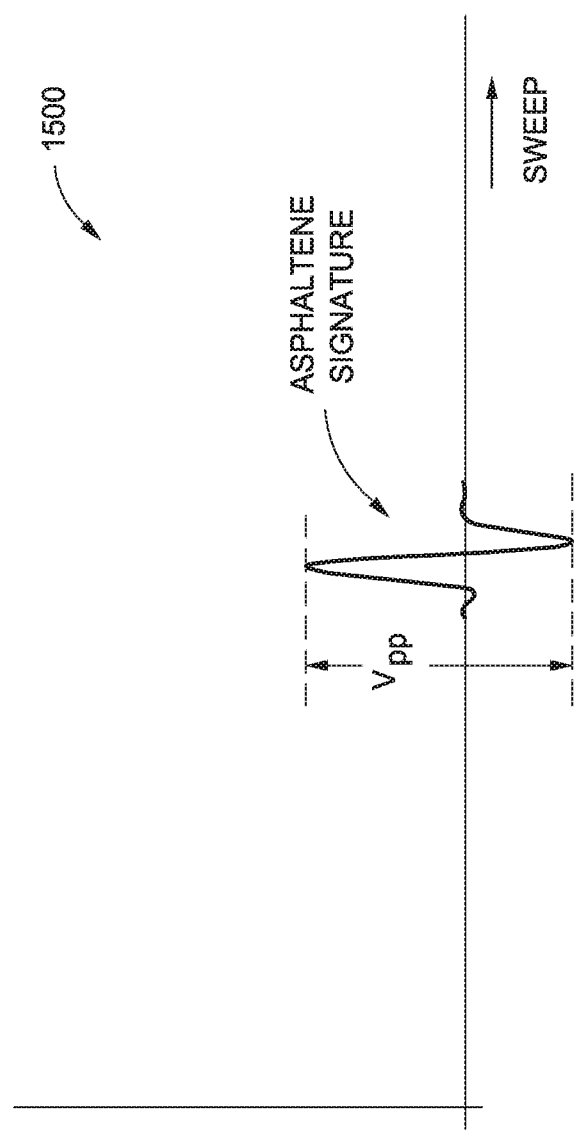
FIG. 15 illustrates an EPR waveform after baseline removal to give a clean peak-to-peak voltage (Vpp) spectrum for a desired component, in accordance with certain aspects of the present disclosure.

Additional signal processing may be appropriate, after the narrower magnetic sweep is complete. For example, one can see from FIG. 13B that a baseline shift may remain on the signal, as indicated by the baseline 1322. This shift may be well approximated as a straight line (i.e., fixed offset plus a slope), and the values of the baseline can be computed from the spectral values near the beginning and end of the sweep. For other aspects, regression analysis of the spectral values may be used to calculate the linear equation for the baseline. Effectively subtracting out this baseline gives the desired asphaltene response as illustrated in the graph 1500 of FIG. 15, which takes the characteristic form of a doublet (e.g., with a zero slope). In this case, the doublet is the derivative of an absorption spectrum that can be characterized in terms of line width, crossing point, and the peak-to-peak voltage (Vpp). Experiments have found good correlation between Vpp and volume of asphaltene. The line width and crossing point of the doublet correlate to chemical properties of the asphaltene. For example, the line width may increase with the geochemical maturity of the asphaltene. For applications related to monitoring cleanout and flow assurance, the Vpp value may be the most useful parameter, together with permittivity or resonance frequency.

Figure 16:
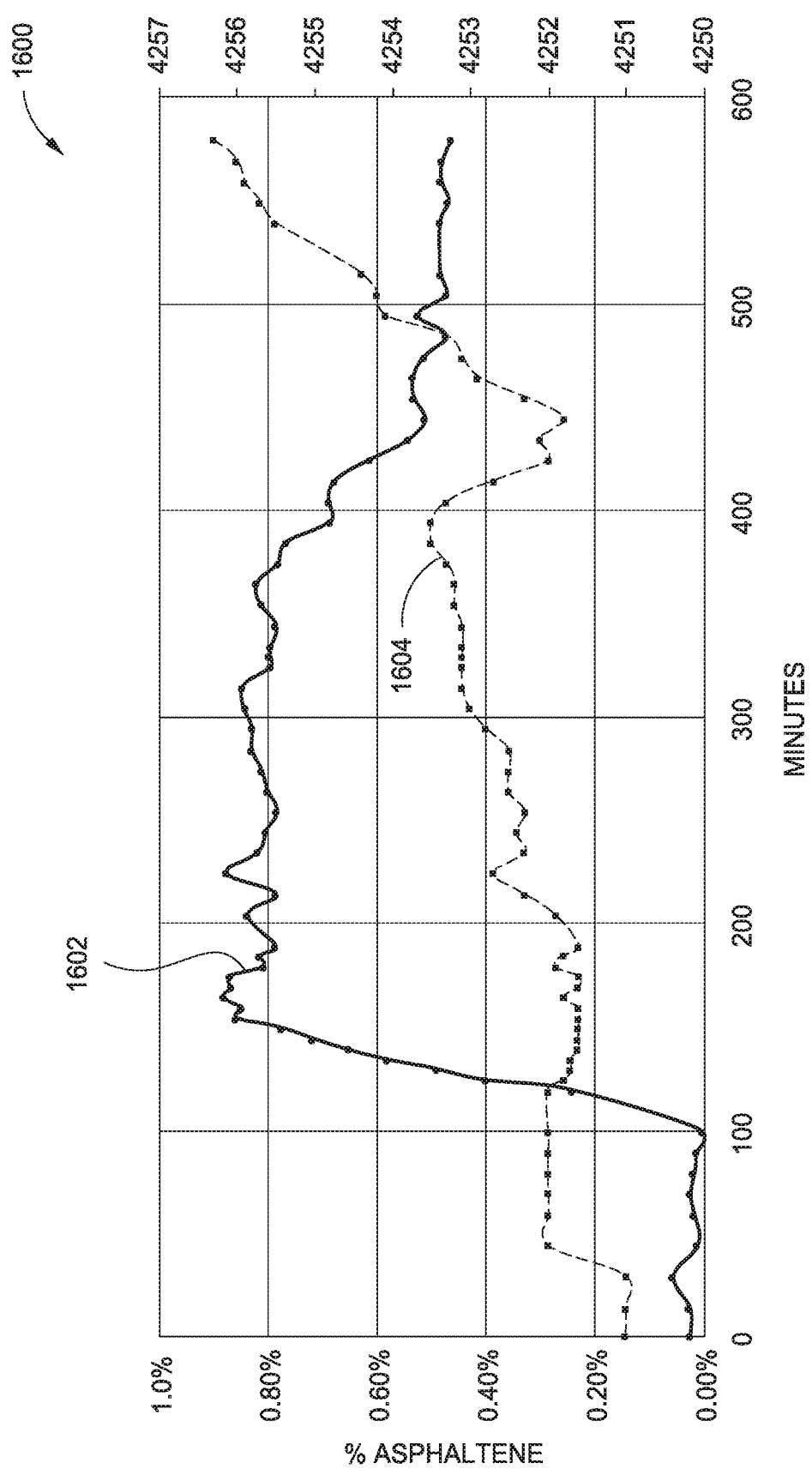
FIG. 16 is an example plot of EPR curves versus time for an EPR spectrometer, in accordance with certain aspects of the present disclosure.

As noted above, for certain aspects, the Vpp value can be computed very quickly (e.g., within a few seconds), so that the final output of the EPR spectrometer becomes a time-series curve of the Vpp values. As an interface for an operator of the EPR spectrometer, the Vpp value versus time can be plotted directly. As an alternative embodiment, such as shown in the plot 1600 of FIG. 16, the Vpp data can be calibrated against the response of reference percentages of asphaltene, in which case the data can then be plotted as a curve 1602 representing a percentage of asphaltene versus time (in minutes). Optional additional curves added to the same plot 1600 may enhance the value of the spectrometer data. For example, in FIG. 16, a curve 1604 for the cavity resonant frequency (in MHz) has been plotted alongside asphaltene percentage for the same time series. Additionally or alternatively, other derived values (6, 6, etc.) may also be plotted.

The above description refers specifically to the identification of asphaltene in crude oil, but a person having ordinary skill in the art will understand these techniques are equally applicable to any EPR spectrometric analysis where a focused magnetic sweep is performed for the paramagnetic target of interest.

The measurements of impedance match, resonant frequency, estimated dielectric, and power transmission/absorption may also be used for quality control. Because these measurements are typically made much faster than the magnetic sweep is performed, it is possible to take such measurements before and after the magnetic sweep. If the values have not changed significantly, then one can have confidence that the fluid properties did not change during the sweep.

The incorporation of fast feedback information into the circuitry of an EPR spectrometer enables continuous EPR logging of a flowing well. The feedback allows the enhanced spectroscope to automatically determine a near resonant frequency of a fluid-filled cavity plumbed into a flow line while also updating RF coupling components so as to optimize, or at least increase, the amplitude of the applied RF magnetic field in the resonator cavity. The values chosen for the excitation frequency and the matching impedance can be incorporated along with the EPR spectrum.

Figure 17:
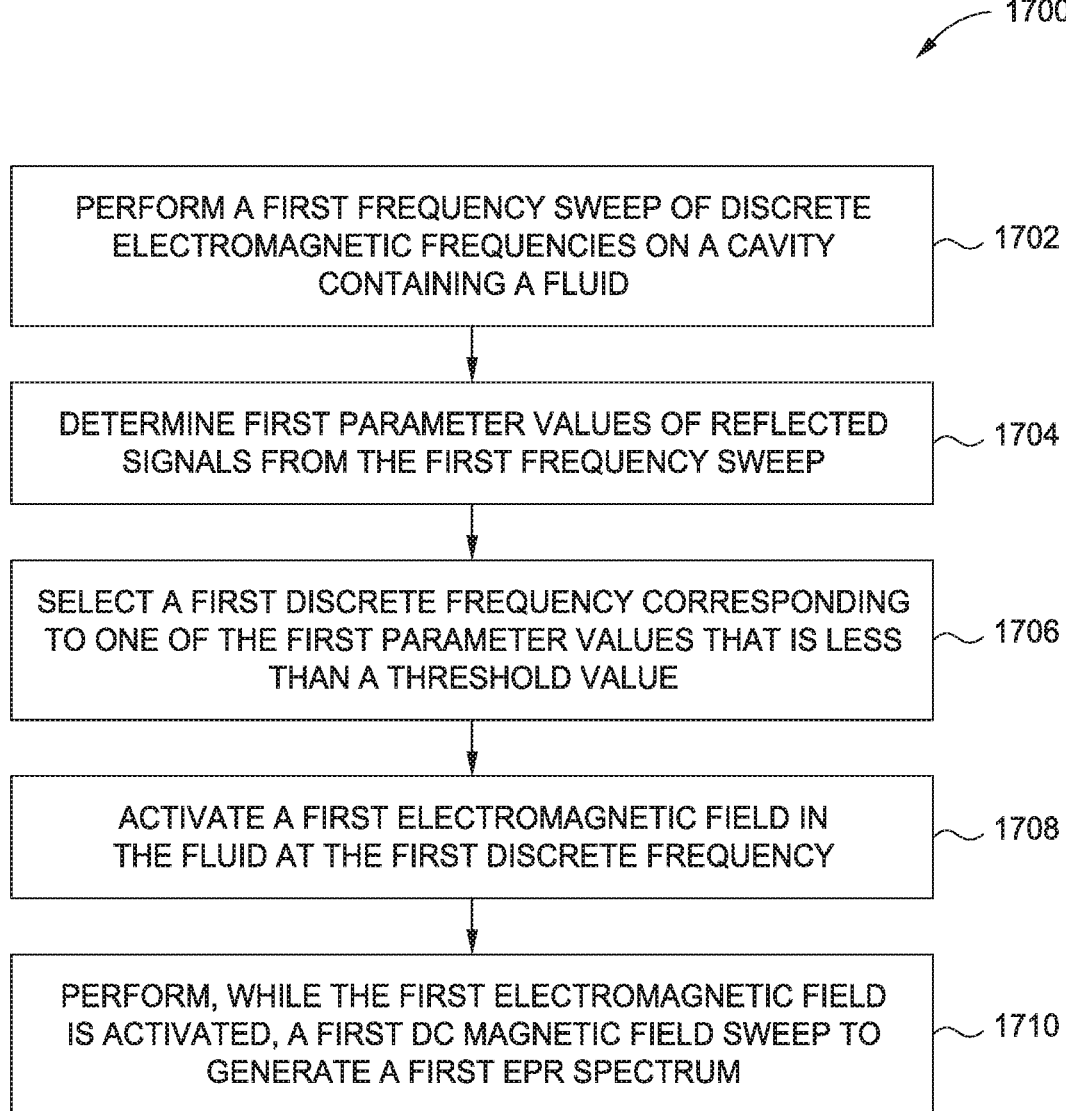
FIGS. 17 and 18 are flow diagrams of example operations for performing EPR spectroscopy on a fluid, in accordance with certain aspects of the present disclosure.

FIG. 17 is a flow diagram of example operations 1700 for performing EPR spectroscopy on a fluid (e.g., from a flowing well), in accordance with certain aspects of the present disclosure. The operations 1700 may be performed, or at least controlled, by a control unit, such as the control unit 902 of FIG. 9.

For a first EPR iteration, the operations may begin, at block 1702, by performing a first frequency sweep of discrete electromagnetic frequencies on a cavity containing the fluid. At block 1704, first parameter values of reflected signals from the first frequency sweep may be determined. The control unit may select, at block 1706, a first discrete frequency corresponding to one of the first parameter values that is less than a threshold value. At block 1708, a first electromagnetic field may be activated in the fluid at the first discrete frequency. While the first electromagnetic field is activated, a first DC magnetic field sweep may be performed at block 1710 to generate a first EPR spectrum.

According to certain aspects, the operations 1700 further involve estimating a first resonant frequency of the cavity containing the fluid for the first EPR iteration. For certain aspects, selecting the first discrete frequency at block 1706 includes selecting one of the discrete electromagnetic frequencies that is at or closest to the estimated first resonant frequency as the first discrete frequency. For certain aspects, the operations 1700 may further entail, for a second EPR iteration subsequent to the first EPR iteration: performing a second frequency sweep of discrete electromagnetic frequencies on the cavity containing the fluid for the second EPR iteration; determining second parameter values of reflected signals from the second frequency sweep; comparing a parameter value of a reflected signal in the second frequency sweep to the threshold value, the parameter value corresponding to the first discrete frequency; activating a second electromagnetic field at the first discrete frequency if the parameter value of the reflected signal in the second frequency sweep is less than the threshold value; and while the second electromagnetic field is activated, performing a second DC magnetic field sweep to generate a second EPR spectrum. For certain aspects, the operations 1700 may further include, for the second EPR iteration if the parameter value of the reflected signal in the second frequency sweep is greater than the threshold value: estimating a second resonant frequency of the cavity containing the fluid for the second EPR iteration based on the second frequency sweep; selecting a second discrete frequency; and activating the second electromagnetic field in the fluid at the second discrete frequency. For certain aspects, selecting the second discrete frequency entails selecting one of the discrete electromagnetic frequencies that is at or closest to the estimated second resonant frequency as the second discrete frequency. For certain aspects, the parameter value of the reflected signal comprises a power of the reflected signal, and the threshold value is a threshold power. For other aspects, the parameter value of the reflected signal is a voltage amplitude of the reflected signal, and the threshold value comprises a threshold voltage amplitude.

According to certain aspects, the operations 1700 further entail performing an impedance matching circuit sweep concurrently with the performance of the first frequency sweep. For other aspects, the impedance matching circuit sweep may be performed sequentially with the performance of the first frequency sweep. In either case, the operations 1700 may further involve at least one of: determining a quality factor (Q) based on at least one of the first frequency sweep or the impedance sweep; determining a dielectric constant based on at least one of the first frequency sweep or the impedance sweep; determining a conductivity of the fluid based on at least one of the first frequency sweep or the impedance sweep; determining a resonant frequency of the cavity based on at least one of the first frequency sweep or the impedance sweep; or determining a composition of the fluid based on at least one of the Q, the dielectric constant, the conductivity, or the resonant frequency.

According to certain aspects, the first frequency sweep is performed in less than 1 ms. For other aspects, the first frequency sweep is performed in less than 1 s.

According to certain aspects, the cavity containing the fluid is in pressure communication with equipment at a wellsite. In this case, the fluid may be exposed to wellbore (or wellhead) pressure and temperature during the performance of the first DC magnetic field sweep. Furthermore, the flowing fluid may not be exposed to extraneous oxygen during conveyance from the equipment to a resonator having the cavity.

Figure 18:
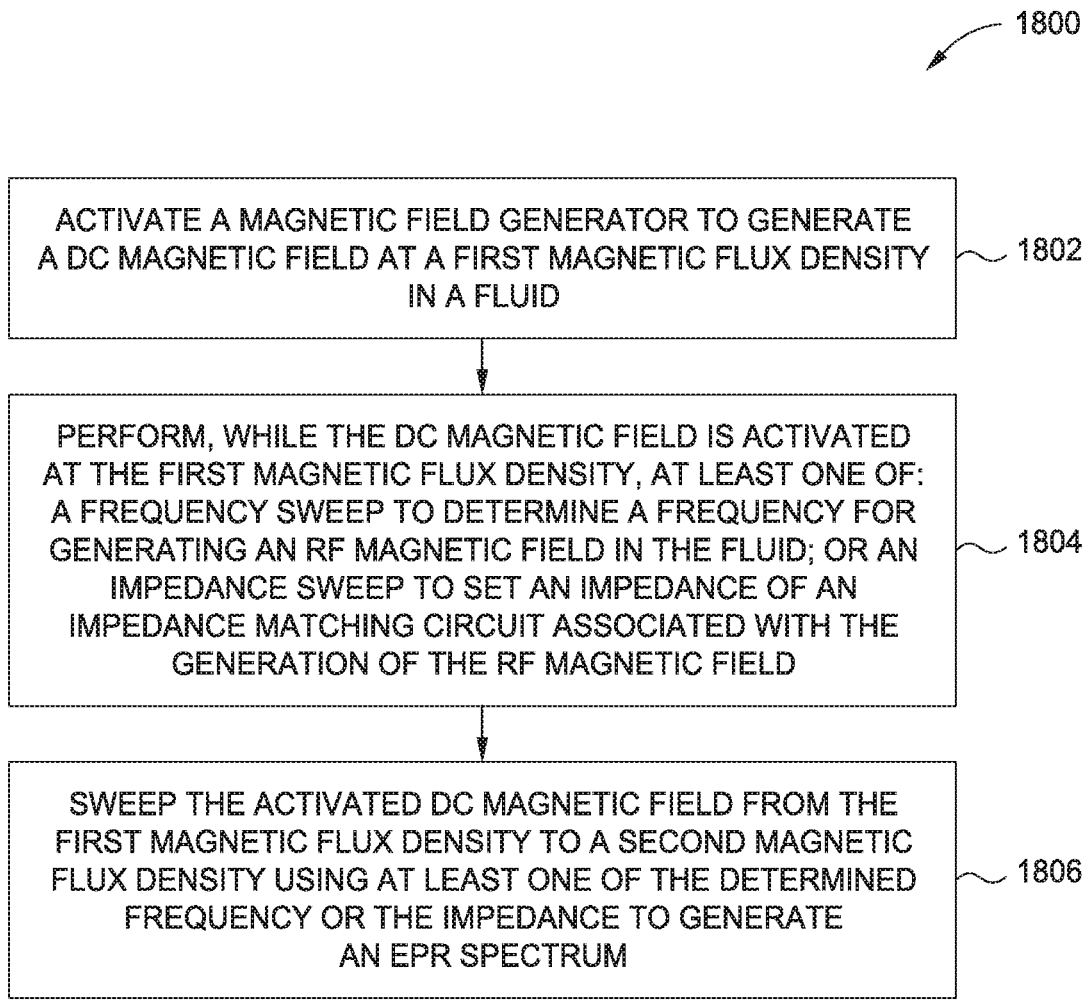

FIG. 18 is a flow diagram of example operations 1800 for performing EPR spectroscopy on a fluid (e.g., from a flowing well), in accordance with certain aspects of the present disclosure. The fluid may be transported to a cavity. The operations 1800 may be performed, or at least controlled, by a control unit, such as the control unit 902 of FIG. 9.

The operations 1800 may begin, at block 1802, by activating a magnetic field generator to generate a DC magnetic field at a first magnetic flux density. The magnetic field may be activated in a cavity containing the fluid. While the DC magnetic field is activated at the first magnetic flux density, at least one of the following may be performed at block 1804: (1) a frequency sweep to determine a frequency for generating a radio frequency (RF) magnetic field in the fluid; or (2) an impedance sweep to set an impedance of an impedance matching circuit associated with the generation of the RF magnetic field. At block 1806, the activated DC magnetic field may be swept from the first magnetic flux density to a second magnetic flux density using at least one of the determined frequency or the impedance to generate an EPR spectrum.

According to certain aspects, a range from the first magnetic flux density to the second magnetic flux density corresponds to a particular paramagnetic material of interest. For certain aspects, the particular paramagnetic material of interest is asphaltene. In this case, the first magnetic flux density is at least 0.15 T, and the second magnetic flux density is at most 0.17 T. Alternatively, a ratio of the first magnetic flux density to the frequency is at least 0.035 T/GHz, and a ratio of the second magnetic flux density to the frequency is at most 0.040 T/GHz.

According to certain aspects, performing the frequency sweep while the DC magnetic field is activated at the first magnetic flux density at block 1804 includes determining a resonant frequency of the fluid and selecting a discrete frequency at or closest to the resonant frequency as the frequency for generating the RF magnetic field.

According to certain aspects, performing the frequency sweep while the DC magnetic field is activated at the first magnetic flux density at block 1804 entails determining a resonant frequency of the fluid. In this case, the operations 1800 may further involve determining a quality factor (Q) based on the frequency sweep. For certain aspects, the operations 1800 may further include at least one of: determining a fluid dielectric constant based on the at least one of the frequency sweep or the impedance sweep, determining a fluid conductivity based on the at least one of the frequency sweep or the impedance sweep, determining a resonant frequency of the cavity containing the fluid, or determining a composition of the fluid based on at least one of the Q, the fluid dielectric constant, the fluid conductivity, or the resonant frequency.

According to certain aspects, the operations 1800 may further involve calculating a regression line based on the EPR spectrum, removing at least the slope of the regression line from the EPR spectrum to generate an adjusted EPR spectrum, and determining a peak-to-peak voltage of the adjusted EPR spectrum.

According to certain aspects, the operations 1800 may further entail repeating the performing at block 1804 and the sweeping at block 1806 to generate a plurality of EPR spectrums; storing at least one of the frequency for each frequency sweep or a parameter indicative of the impedance setting for each impedance sweep; determining a plurality of peak-to-peak voltages based on the plurality of EPR spectrums; and plotting the plurality of peak-to-peak voltages versus time and the at least one of the stored frequencies or the stored impedances versus time. For example, the parameter indicative of the impedance setting may be a voltage for a varactor (or a digital value for a switched capacitor or switched array of capacitors) in the impedance matching circuit.

According to certain aspects, the operations 1800 may further include after the sweeping at block 1806, performing at least one of another frequency sweep to determine at least one of another frequency or another impedance sweep to set another impedance; comparing at least one of the frequency with the other frequency or the impedance with the other impedance; and determining whether one or more properties of the fluid changed during the sweeping of the activated DC magnetic field based on the comparison.

According to certain aspects, a cavity containing the fluid is in pressure communication with equipment at a wellsite. In this case, the fluid may be exposed to wellhead (or wellbore) pressure and temperature during the sweeping of the activated DC magnetic field. Furthermore, the fluid may not be exposed to extraneous oxygen during conveyance from the equipment to a resonator having the cavity.

Certain aspects of the present disclosure provide an EPR spectrometer for performing EPR spectroscopy on a fluid from a flowing well. The EPR spectrometer generally includes a tube capable of receiving the fluid; a magnetic field generator configured to generate a DC magnetic field in the fluid during operation of the EPR spectrometer; transmit circuitry configured to generate a radio frequency (RF) signal; a resonator coupled to the transmit circuitry and configured to convert the RF signal into an RF magnetic field in the fluid during the operation of the EPR spectrometer; impedance matching circuitry coupled between the transmit circuitry and the resonator; receive circuitry configured to receive and process reflected signals from the fluid via the resonator; and at least one processor coupled to the magnetic field generator, the transmit circuitry, and the receive circuitry. The at least one processor is generally configured to activate the magnetic field generator to generate the DC magnetic field at a first magnetic flux density; to control, while the DC magnetic field is activated at the first magnetic flux density, at least one of: (1) the transmit circuitry to perform a frequency sweep to determine a frequency for generating the RF magnetic field in the fluid; or (2) the impedance matching circuitry to perform an impedance sweep to set an impedance of the impedance matching circuitry associated with the generation of the RF magnetic field; and to control the magnetic field generator to sweep the activated DC magnetic field from the first magnetic flux density to a second magnetic flux density using at least one of the determined frequency or the impedance to generate an EPR spectrum.

According to certain aspects, a range from the first magnetic flux density to the second magnetic flux density corresponds to a particular paramagnetic material of interest. For example, the particular paramagnetic material of interest is asphaltene. In this case, the first magnetic flux density may be 0.15 T, and the second magnetic flux density may be 0.17 T (e.g., for the determined frequency in a range from 3 to 5 GHz).

According to certain aspects, the at least one processor is configured to control the transmit circuitry to perform the frequency sweep while the DC magnetic field is activated at the first magnetic flux density by determining a resonant frequency of the fluid and selecting a discrete frequency at or closest to the resonant frequency as the frequency for generating the RF magnetic field.

According to certain aspects, the at least one processor is configured to control the transmit circuitry to perform the frequency sweep while the DC magnetic field is activated at the first magnetic flux density by determining a resonant frequency of the fluid. In this case, the at least one processor may be further configured to determine a quality factor (Q) based on the frequency sweep. For certain aspects, the at least one processor is further configured to determine a dielectric constant based on the resonant frequency; to determine a conductivity of the fluid based on the quality factor; to calculate a complex permittivity based on the dielectric constant and the conductivity; and to determine a composition of the fluid based on the complex permittivity.

According to certain aspects, the at least one processor is further configured to calculate a baseline (e.g., a regression line) based on the EPR spectrum, to remove at least the slope of the baseline from the EPR spectrum to generate an adjusted EPR spectrum, and to determine a peak-to-peak voltage of the adjusted EPR spectrum.

In one aspect, components of an enhanced EPR spectrometer may comprise a resonator surrounding a cylindrical cavity through which pressurized well-fluids can flow, an RF transceiver with at least one variable component to couple RF energy to the resonator, a mechanism to measure the efficiency of the coupling, a magnetic field generator with adjustable magnetic field, and a feedback loop to update the coupling based on the properties of the fluid as the fluid enters the cavity. The spectrometer may use a circulator to measure the reflected microwave power from the resonator.

Further, the resonator may be a loop-gap resonator with a loop perpendicular to the cavity axis. The magnetic field generator may produce a magnetic field, more particularly a DC magnetic field. The magnetic field generator may comprise magnets, coils, or a combination thereof that are positioned exterior to the cavity to generate a magnetic field therein. The transceiver of the EPR spectrometer may provide a pulsed or continuous signal to the resonator to generate a pulsed or continuous RF magnetic field approximately normal to the DC magnetic field of the magnets or coils. A receiver of the EPR spectrometer may monitor a reflected signal to detect changes in reflected signal. The frequency of RF transmission may be changed as may be the variable component in the coupling from the transceiver to the resonator. These changes may be changed as part of individual feedback loops or simultaneously as part of a dual feedback loop. The RF frequency may be chosen to be near the resonance frequency of the cavity. The strength of the DC magnetic field may be swept. A modulation frequency may be further superimposed on that sweep. The initiation of that magnetic field sweep may be triggered by a range of values of the chosen frequency or coupling component. The changes in the reflected signal based on the changing DC field, the RF frequency, and the coupling component may be analyzed to determine the materials present and material concentrations.

Any of the operations described above, such as the operations 1100, 1200, 1400, 1700, and/or 1800 may be included as instructions in a computer-readable medium for execution by a control unit (e.g., control unit 902 or controller module 706) or any other processing system. The computer-readable medium may comprise any suitable memory for storing instructions, such as read-only memory (ROM), random access memory (RAM), flash memory, an electrically erasable programmable ROM (EEPROM), a compact disc ROM (CD-ROM), a floppy disk, and the like.

While the foregoing is directed to certain aspects of the present disclosure, other and further aspects may be devised without departing from the basic scope thereof, and the scope thereof is determined by the claims that follow.

The invention claimed is:

1. A method of performing electron paramagnetic resonance (EPR) spectroscopy on a fluid from a flowing well, the method comprising, for a first EPR iteration:
   performing a first frequency sweep of discrete electromagnetic frequencies on a cavity containing the fluid;
   determining first parameter values of reflected signals from the first frequency sweep;
   selecting a first discrete frequency corresponding to one of the first parameter values that is less than a threshold value;
   activating a first electromagnetic field in the fluid at the first discrete frequency; and
   while the first electromagnetic field is activated, performing a first DC magnetic field sweep to generate a first EPR spectrum.

2. The method of claim 1, further comprising estimating a first resonant frequency of the cavity containing the fluid for the first EPR iteration.

3. The method of claim 2, wherein selecting the first discrete frequency comprises selecting, as the first discrete frequency, one of the discrete electromagnetic frequencies that is at or closest to the estimated first resonant frequency.

4. The method of claim 2, further comprising, for a second EPR iteration subsequent to the first EPR iteration:
   performing a second frequency sweep of discrete electromagnetic frequencies on the cavity containing the fluid for the second EPR iteration;
   determining second parameter values of reflected signals from the second frequency sweep;
   comparing a parameter value of a reflected signal in the second frequency sweep to the threshold value, the parameter value corresponding to the first discrete frequency;
   activating a second electromagnetic field at the first discrete frequency if the parameter value of the reflected signal in the second frequency sweep is less than the threshold value; and
   while the second electromagnetic field is activated, performing a second DC magnetic field sweep to generate a second EPR spectrum.

5. The method of claim 4, further comprising, for the second EPR iteration if the parameter value of the reflected signal in the second frequency sweep is greater than the threshold value:
  estimating a second resonant frequency of the cavity containing the fluid for the second EPR iteration based on the second frequency sweep;
  selecting a second discrete frequency; and
  activating the second electromagnetic field in the fluid at the second discrete frequency.

6. The method of claim 5, wherein selecting the second discrete frequency comprises selecting, as the second discrete frequency, one of the discrete electromagnetic frequencies that is at or closest to the estimated second resonant frequency.

7. The method of claim 4, wherein the parameter value of the reflected signal comprises a power of the reflected signal and wherein the threshold value comprises a threshold power.

8. The method of claim 4, wherein the parameter value of the reflected signal comprises a voltage amplitude of the reflected signal and wherein the threshold value comprises a threshold voltage amplitude.

9. The method of claim 1, further comprising performing an impedance sweep with an impedance matching circuit concurrently with the performance of the first frequency sweep.

10. The method of claim 9, further comprising at least one of:
  determining a quality factor (Q) based on at least one of the first frequency sweep or the impedance sweep;
  determining a dielectric constant based on at least one of the first frequency sweep or the impedance sweep;
  determining a conductivity of the fluid based on at least one of the first frequency sweep or the impedance sweep;
  determining a resonant frequency of the cavity based on at least one of the first frequency sweep or the impedance sweep; or
  determining a composition of the fluid based on at least one of the Q, the dielectric constant, the conductivity, or the resonant frequency.

11. The method of claim 1, wherein the first frequency sweep is performed in less than 1 ms.

12. The method of claim 1, wherein the first frequency sweep is performed in less than 1 s.

13. The method of claim 1, wherein:
  the cavity containing the fluid is in pressure communication with equipment at a wellsite;
  the fluid is exposed to wellbore or wellhead pressure at the wellsite during the performance of the first DC magnetic field sweep; and
  the fluid is not exposed to extraneous oxygen during conveyance from the equipment to a resonator having the cavity.

14. An electron paramagnetic resonance (EPR) spectrometer for performing EPR spectroscopy on a fluid from a flowing well, the EPR spectrometer comprising:
  a tube having a cavity capable of receiving the fluid;
  a magnetic field generator configured to generate a DC magnetic field in the fluid during operation of the EPR spectrometer;
  transmit circuitry configured to generate a radio frequency (RF) signal;
  a resonator coupled to the transmit circuitry and configured to convert the RF signal into an RF magnetic field in the fluid during the operation of the EPR spectrometer;
  receive circuitry configured to receive and process reflected signals from the fluid via the resonator; and
  at least one processor coupled to the magnetic field generator, the transmit circuitry, and the receive circuitry and configured, for a first EPR iteration, to:
    control the transmit circuitry to perform a first frequency sweep of discrete electromagnetic frequencies on the cavity containing the fluid;
    determine first parameter values of reflected signals from the first frequency sweep;
    select a first discrete frequency corresponding to one of the first parameter values that is less than a threshold value;
    control the transmit circuitry to activate a first electromagnetic field in the fluid at the first discrete frequency; and
    control the magnetic field generator, while the first electromagnetic field is activated, to perform a first DC magnetic field sweep to generate a first EPR spectrum.

15. The EPR spectrometer of claim 14, wherein the at least one processor is further configured to estimate a first resonant frequency of the cavity containing the fluid for the first EPR iteration.

16. The EPR spectrometer of claim 15, wherein the at least one processor is configured to select the first discrete frequency by selecting, as the first discrete frequency, one of the discrete electromagnetic frequencies that is at or closest to the estimated first resonant frequency.

17. The EPR spectrometer of claim 15, wherein the at least one processor is further configured, for a second EPR iteration subsequent to the first EPR iteration, to:
  control the transmit circuitry to perform a second frequency sweep of discrete electromagnetic frequencies on the cavity containing the fluid for the second EPR iteration;
  determine second parameter values of reflected signals from the second frequency sweep;
  compare a parameter value of a reflected signal in the second frequency sweep to the threshold value, the parameter value corresponding to the first discrete frequency;
  control the transmit circuitry to activate a second electromagnetic field at the first discrete frequency if the parameter value of the reflected signal in the second frequency sweep is less than the threshold value; and
  control the magnetic field generator, while the second electromagnetic field is activated, to perform a second DC magnetic field sweep to generate a second EPR spectrum.

18. The EPR spectrometer of claim 17, wherein the at least one processor is further configured, for the second EPR iteration if the parameter value of the reflected signal in the second frequency sweep is greater than the threshold value, to:
  estimate a second resonant frequency of the cavity containing the fluid for the second EPR iteration based on the second frequency sweep;
  select a second discrete frequency; and
  control the transmit circuitry to activate the second electromagnetic field in the fluid at the second discrete frequency.

19. The EPR spectrometer of claim 14, wherein the tube is positioned to have a longitudinal axis at least one of perpendicular to the DC magnetic field or parallel to the RF magnetic field.

20. A non-transitory computer-readable medium storing instructions that, when executed on a processor, perform operations for performing electron paramagnetic resonance (EPR) spectroscopy on a fluid from a flowing well, the operations comprising, for an EPR iteration:
- performing a frequency sweep of discrete electromagnetic frequencies on a cavity containing the fluid;
- determining parameter values of reflected signals from the frequency sweep;
- selecting a discrete frequency corresponding to one of the parameter values that is less than a threshold value;
- activating an electromagnetic field in the fluid at the discrete frequency; and
- while the electromagnetic field is activated, performing a DC magnetic field sweep to generate an EPR spectrum.

* * * * *